United States Patent
Olichon et al.

(10) Patent No.: US 11,319,381 B2
(45) Date of Patent: May 3, 2022

(54) ANTI-RHO GTPASE CONFORMATIONAL SINGLE DOMAIN ANTIBODIES AND USES THEREOF

(71) Applicants: INSERM (Institut National de la Sante et de la Recherche Medicale), Paris (FR); Universite Paul Sabatier Toulouse III, Toulouse (FR); Institut Claudius Regaud, Toulouse (FR)

(72) Inventors: Aurelien Olichon, Toulouse (FR); Laura Keller, Toulouse (FR); Gilles Favre, Toulouse (FR); Nicolas Bery, Toulouse (FR); Patrick Chinestra, Toulouse (FR)

(73) Assignees: INSERM (Institut National de la Santéet de la Recherche Médicale), Paris (FR); UniversitéPaul Sabatier Toulouse III, Toulouse (FR); Institut Claudius Regaud, Toulouse (FR)

( * ) Notice: Subject to any disclaimer, the term of this patent is extended or adjusted under 35 U.S.C. 154(b) by 317 days.

(21) Appl. No.: 16/703,343

(22) Filed: Dec. 4, 2019

(65) Prior Publication Data

US 2021/0171658 A1 Jun. 10, 2021

Related U.S. Application Data

(62) Division of application No. 15/548,578, filed as application No. PCT/EP2016/052136 on Feb. 2, 2016, now Pat. No. 10,544,210.

(30) Foreign Application Priority Data

Feb. 3, 2015 (EP) .................................... 15305160

(51) Int. Cl.
*C07K 16/40* (2006.01)
*C12N 15/85* (2006.01)
*C12N 15/11* (2006.01)
*C12N 15/13* (2006.01)
*C12N 15/09* (2006.01)

(52) U.S. Cl.
CPC .............. *C07K 16/40* (2013.01); *C12N 15/85* (2013.01); *C07K 2317/565* (2013.01); *C07K 2317/567* (2013.01); *C07K 2317/569* (2013.01); *C07K 2317/76* (2013.01); *C07K 2317/80* (2013.01); *C07K 2319/95* (2013.01); *C12N 2015/8518* (2013.01)

(58) Field of Classification Search
None
See application file for complete search history.

(56) References Cited

U.S. PATENT DOCUMENTS 10,544,210 B2 * 1/2020 Olichon .................. A61P 35/00

* cited by examiner

*Primary Examiner* — Gary B Nickol
*Assistant Examiner* — Jegatheesan Seharaseyon
(74) *Attorney, Agent, or Firm* — WCF IP

(57) ABSTRACT

The present invention relates to active form specific anti-Rho GTPase conformational single domain antibodies and their uses in particular in the therapeutic and diagnostic fields. In particular, the present invention relates to a single domain antibody wherein the amino acid sequences of CDR1-IMGT, CDR2-IMGT and CDR3-IMGT have at least 90% of identity with the amino acid sequences of the CDR1-IMGT, CDR2-IMGT and CDR3-IMGT of the H12, B6, 4P75, 4SP1, 4SNP36, 4SNP61, 5SP10, 5SP11, 5SP58, 5SNP47, 5SNP48, 5SNP65, B20, B15, B5, B71, E3, A6, G12, NB61, 212B, 111B or 404F (hs2dAb) single domain antibody which are defined in Table B.

3 Claims, 9 Drawing Sheets

Figure 2:
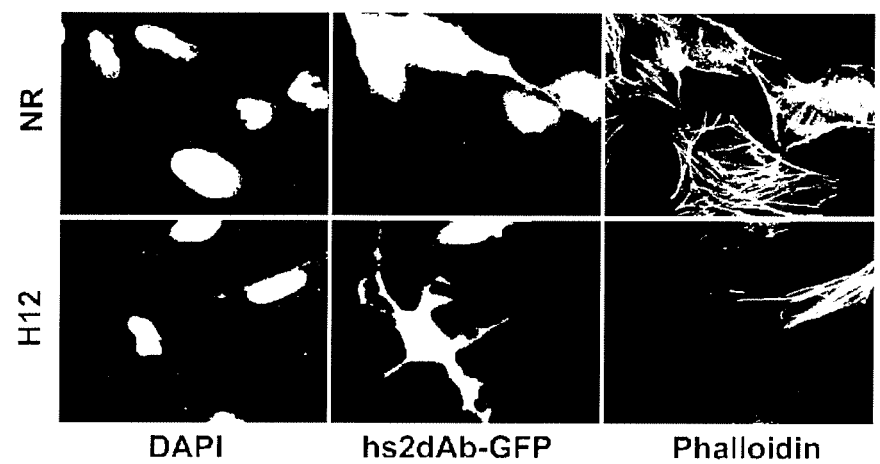

Specification includes a Sequence Listing.

Figure 1A
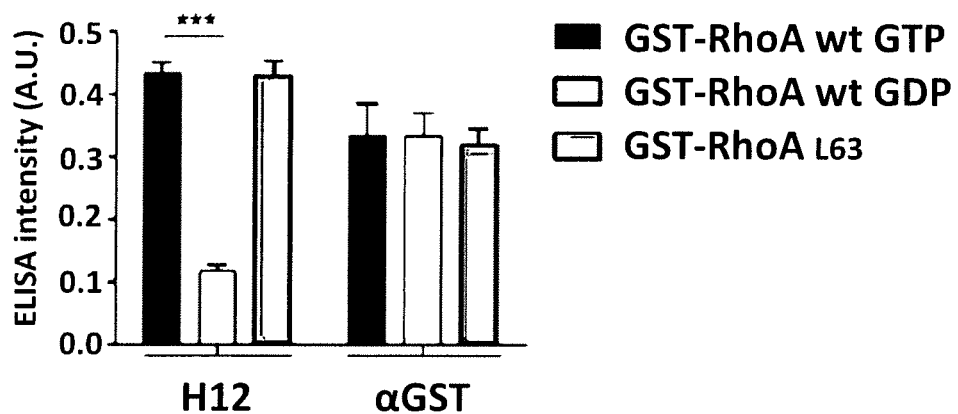
Figure 1B
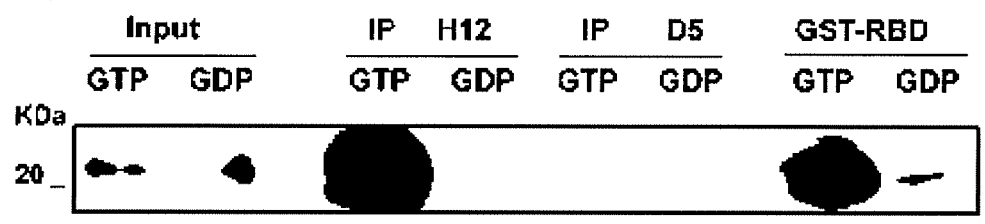
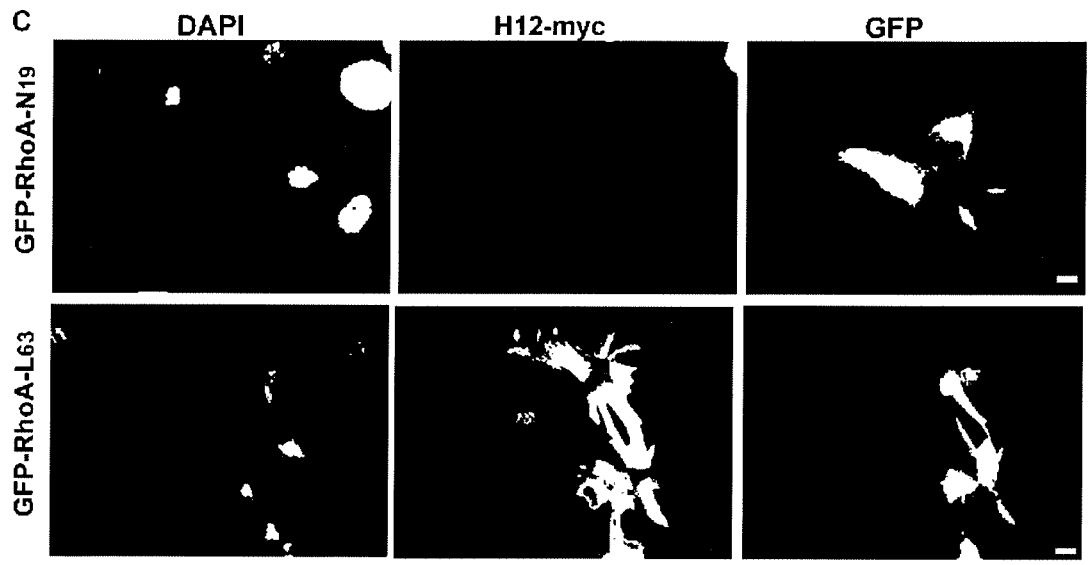
Figure 1C

US 11,319,381 B2

ANTI-RHO GTPASE CONFORMATIONAL SINGLE DOMAIN ANTIBODIES AND USES THEREOF

FIELD OF THE INVENTION

The present invention relates to anti-Rho GTPase conformational single domain antibodies and their uses thereof in particular in the therapeutic and diagnostic fields.

BACKGROUND OF THE INVENTION

Rho GTPases belong to the family of the 20 small GTPases homologous to Ras which are largely considered as undrugable proteins. Their physiologic activity resides more in a conformational change of the switch I and switch II highly conserved domains than in their guanine nucleotide triphosphate hydrolase very slow catalytic activity. Small G proteins are therefore molecular switch that cycle between an inactive GDP bound state an active GTP bound conformation. The Rho subfamily, which contains RhoA, RhoB and RhoC that share more than 85% sequence identities are pleiotropic proteins involved in a wide range of major cell processes, including the control of actomyosin cytoskeleton, cell adhesion, cytokinesis, cell migration, stress response as well as cell survival or apoptosis. These GTPases are post-translationally modified by addition of a carboxy terminal isoprenoid group necessary for their anchorage to cellular membranes, where they can be activated upon various stimuli by an exchange of nucleotide catalyzed by Guanine nucleotide Exchange Factors (GEF). Activation step is then counterbalanced by GTP hydrolyses which is enhanced by GTPase Activating Proteins (GAPs). Therefore the cellular pool of activated Rho is maintained at the cellular membrane to limited pool. The major fraction is extracted from the membrane and sequestered in the cytoplasm by Guanine nucleotide Dissociation Inhibitors (GDI). These large proteins interact by their amino terminal part with the switch domains of Rho, thus preventing the release of the GDP, and also by their carboxy terminal part to the isoprenyl group, shielding this hydrophobic moiety in order to maintain the Rho proteins soluble while excluded from membranes.

Together these regulators maintain the largest fraction of Rho Proteins inactive in the cell, often as much as 95%, in order to quickly activate a very small population that will interact with effector proteins to initiate cellular transduction pathways. Moreover study of the crosstalk between the 3 GDI and all interacting Rho revealed that overexpression of a single Rho can induce artificially displacement and degradation of others and impair signaling pathways not directly controlled by the transgene. This critical point highlights the complexity of targeting individual Rho in a selective manner.

The peculiar RhoB seems to be involved in different cellular functions and regulations than its closest homologs RhoA and RhoC. RhoB can be palmitoylated and either farnesylated or geranylgeranylated, prenylation which define localization to the plasma membrane or the endosome respectively. Some main RhoB functions in intracellular trafficking and adhesion have been characterized using conventional molecular tools such as overexpression of wild type or mutants or genetic knock down by RNA interference. Other functions have been connected to RhoB gene expression as an immediate early response to cytokines or growth factors as well as DNA damaging agent or radiation. In addition, RhoB plays paradoxal roles in cancer progression. RhoB can alter tumor formation and is often down regulated in head and neck or lung cancers.

Nevertheless RhoB is also promoting tumor angiogenesis and protecting from apoptosis in cells with genomic instability. There are now clear evidences that RhoB exert pleiotropic functions which are cells and context dependent. Previous studies targeted RhoB at the genetic level by overexpression, RNAi or gene knock out in mice. However these methods altered RhoB functions in a global way, knocking down all RhoB activities in cells, but mostly altering both the GDP bound major fraction which can induce imbalances in the GDI-Rho interactions and the minor GTP bound active pool. To decipher RhoB function without interfering with other Rho activities, it would be necessary to target RhoB at the protein level. Albeit there are no small molecule inhibitors targeting Rho GTPases, the C3 exoenzyme from *Claustridium botulinum* or *Bacillus cereus* are natural inhibitors that induce ADP-ribosylation of Rho, preventing their activation by GEF and further increasing the binding of free Rho to GDI. Actually expression of C3 gene in eukaryotic cells or incubation with cell permeable tat-C3 has been successfully used to alter globally the function of all 3 Rho, leading to a strong phenotype of actin fiber loss and cell rounding. Several other bacterial toxin target as well Rho proteins. Nevertheless all these toxins lack specificity because they do not discriminate between RhoA, RhoB or RhoC and mostly do not block directly the activated form of Rho.

In some previous studies, the selection of recombinant single chain antibodies from phage display libraries was established in order to identify binding molecules selective to the active GTP bound state of Rho proteins. Actually recombinant antibody selected from large display libraries have been used in many biotechnological or biomedical applications. Although most of recombinant antibodies require for stability the canonical disulfide bond within the VH or VL variable domains, some peculiar intracellular antibodies, referred as intrabodies, remains stable in the reducing environment. Thus, depending on the antibody format, the scaffold properties and the library diversities, some rare recombinant antibodies have been reported to be functional while expressed in the cytosol of eukaryotic cells (Tanaka, T., Williams, R. L. & Rabbitts, T. H. Tumour prevention by a single antibody domain targeting the interaction of signal transduction proteins with RAS. EMBO J 26, 3250-3259, doi:7601744 [pii] 10.1038/sj.emboj.7601744 (2007); Nizak, C. et al. Recombinant antibodies to the small GTPase Rab6 as conformation sensors. Science 300, 984-987, doi:10.1126/science.1083911 (2003).; Meli, G., Visintin, M., Cannistraci, I. & Cattaneo, A. Direct in vivo intracellular selection of conformation-sensitive antibody domains targeting Alzheimer's amyloid-beta oligomers. J Mol Biol 387, 584-606, doi:10.1016/j.jmb.2009.01.061 (2009)). The first active Rho conformational single chain variable fragment (scFv), named scFvC1, recognized in vitro in biochemical assays the GTP bound state of all 3 Rho (Goffinet, M. et al. Identification of a GTP-bound Rho specific scFv molecular sensor by phage display selection. BMC Biotechnol 8, 34, doi:1472-6750-8-34 [pii] 10.1186/1472-6750-8-34 (2008).). A molecular evolution of scFvC1 led to the identification of the scFvF7, a higher affinity pan active Rho binder than scFvC1, as well as the scFvE3 that preferentially recognizes active RhoB but is not functional as an intrabody.

SUMMARY OF THE INVENTION

The present invention relates to active form specific anti-Rho GTPase conformational single domain antibodies and their uses in particular in the therapeutic and diagnostic fields. In particular, the present invention is defined by the claims.

DETAILED DESCRIPTION OF THE INVENTION

The inventors produced a fully synthetic library of humanized nanobodies, common name of single domain VH from camelidae. This novel phage display library, based on a unique scaffold optimized for stability, allowed the systematic selection of highly functional binding molecules, which correspond to humanized synthetic single domain antibodies (hs2dAb). The inventors thus especially selected towards various targets several functional intrabodies, among which one conformational sensor of the active GTP bound state of Rho proteins, a clone referred as H12 hs2dAb. They demonstrated that the H12 hs2dAb is a pan Rho binder that do not discriminate between the Rho subfamily members RhoA, RhoB and RhoC, and also bond members of the close Rac1 family of Ras homologous small G proteins. The inventors further isolated by using more competitive selection scheme several active Rho selective hs2dAb molecules with more specificity towards the Rho subfamily, namely that do not recognize Rac1 or other small G proteins. They demonstrated that some of these hs2dAb had sub-nanomolar affinities towards recombinant constitutively active L63 mutant of Rhos. Intracellular expression of these molecules lead to a clear reorganization of actin cytoskeleton, suggesting that they act as strong intracellular inhibitor of Rho signaling in cultured cells. Then the inventors applied the same strategy to select single domain antibodies specific that recognized RhoB in its GTP bound state. In particular, they established a visual in-cell screening of functionalized intrabodies that can induce active RhoB protein knock down. The protein knock down was based on the use of an Fbox domain genetically fused to the selected single domain antibodies, which induce ubiquitination of the bound target and subsequent proteasome dependent degradation. A dual challenge was to identify an intrabody which can physiologically discriminate RhoB from the closest homologs while being selective of the active GTP-bound state. Using cell lines expressing various Rho mutants, the inventors succeeded in selecting a robust genetically encoded RhoB inhibitor selective of its active state and demonstrated the efficiency of this unique tool to knock down endogenous RhoB active fraction, not only depleting its basal activity but also blocking its cellular activation after growth factor treatment. Furthermore, in a proof of principle study the inventors demonstrated that subtle RhoB activity knock down did not displace the whole cellular fraction of RhoB but induced similar phenotype as RNAi on human bronchial epithelial cells migration and invasion. Accordingly, the present invention relates to anti-Rho GTPase conformational single domain antibodies and their uses in particular in the therapeutic and diagnostic fields.

As used herein the term "Rho-GTPase" has its general meaning in the art and refers to the Rho (ras homology) family of small molecular weight guanosine triphosphatases Rho GTPases are molecular switches that control signaling pathways regulating cytoskeleton organization, gene expression, cell cycle progression, cell motility and other cellular processes (Cell Communication and Signaling, 2010, 8, 23). Rho family GTPases are important signaling proteins that control diverse cellular functions related to cancer development, including actin cytoskeleton organization, transcription regulation, cell cycle progression, apoptosis, vesicle trafficking, and cell-to-cell and cell-to-extracellular matrix adhesions (Cell Communication and Signaling, 2010, 8 (23), 1-14; Genes Dev., 1997, 1 1, 2295-2322). In particular, Rho-GTPase includes RhoA, RhoB and RhoC.

The single domain antibodies generated by the inventors are specific for at least one Rho-GTPase, and more particularly for only one Rho-GTPase (e.g. the"B6" hs2dAb is specific for RhoB). However some antibodies of the present invention are able to interact with several Rho-GTPases (e.g. the H12 hs2dAb has affinity for RhoA, RhoB and RhoC as well as Rac1). Accordingly, the single domain antibodies of the present invention are characterized by one or more functional properties such that they are humanized, they have a specific affinity for one Rho-GTPase or for several Rho-GTPases, they are specific for one activated form of the Rho-GTPase (i.e. conformational), they are able to inhibit the activated form of the Rho-GTPase, they are highly stable single domain antibodies, they present high affinity, and they are active in the intracellular environment.

As used herein the term "single domain antibody" has its general meaning in the art and refers to the single heavy chain variable domain of antibodies of the type that can be found in Camelid mammals which are naturally devoid of light chains. Such single domain antibody are also "Nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388. The amino acid sequence and structure of a single domain antibody can be considered to be comprised of four framework regions or "FRs" which are referred to in the art and herein as "Framework region 1" or "FR1"; as "Framework region 2" or "FR2"; as "Framework region 3" or "FR3"; and as "Framework region 4" or "FR4" respectively; which framework regions are interrupted by three complementary determining regions or "CDRs", which are referred to in the art as "Complementarity Determining Region for "CDR1"; as "Complementarity Determining Region 2" or "CDR2" and as "Complementarity Determining Region 3" or "CDR3", respectively. Accordingly, the single domain antibody can be defined as an amino acid sequence with the general structure: FR1-CDR1-FR2-CDR2-FR3-CDR3-FR4 in which FR1 to FR4 refer to framework regions 1 to 4 respectively, and in which CDR1 to CDR3 refer to the complementarity determining regions 1 to 3. In the context of the invention, the amino acid residues of the single domain antibody are numbered according to the general numbering for VH domains given by the IMGT numbering system (Lefranc M.-P., "Unique database numbering system for immunogenetic analysis" Immunology Today, 18, 509 (1997)). The IMGT unique numbering has been defined to compare the variable domains whatever the antigen receptor, the chain type, or the species (Lefranc M.-P., "Unique database numbering system for immunogenetic analysis" Immunology Today, 18, 509 (1997); Lefranc M.-P., "The IMGT unique numbering for Immunoglobulins, T cell receptors and Ig-like domains" The Immunologist, 7, 132-136 (1999).; Lefranc, M.-P., Pommie, C., Ruiz, M., Giudicelli, V., Foulquier, E., Truong, L., Thouvenin-Contet, V. and Lefranc, G., "IMGT unique numbering for immunoglobulin and T cell receptor variable domains and Ig superfamily V-like domains" Dev. Comp. Immunol., 27, 55-77 (2003).). In the IMGT unique numbering, the conserved amino acids always have the same position, for instance cysteine 23, tryptophan 41, hydrophobic amino acid 89, cysteine 104, phenylalanine or tryptophan 118. The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths become crucial information. Gaps in the CDR1-IMGT and CDR2-IMGT (less than 12 and 10 amino acid long, respectively) are put at the top of the CDR-IMGT loops. For instance, when the length of CDR1-IMGT is 7 amino acids, it comprises the positions 27, 28, 29, 30, 36, 37 and 38. When the length of CDR2-IMGT is 7 amino acids, it comprises the positions 56, 57, 58, 59, 63, 64, and 65. The basic length of a rearranged CDR3-IMGT is 13 amino acids (positions 105 to 117), which corresponds to a JUNCTION of 15 amino acids (2nd-CYS 104 to J-TRP or J-PHE 118). This length and corresponding numbering were chosen since they are convenient to use. Indeed, 80% of the IG and TR rearranged sequences in IMGT/LIGM-DB have a CDR3-IMGT length less than or equal to 13 amino acids. If the CDR3-IMGT length is less than 13 amino acids, gaps are created from the top of the loop, in the following order 111, 112, 110, 113, 109, 114, etc. Accordingly, when the length of CDR3-IMGT is 9 amino acids, it comprises the positions 105; 106; 107; 108; 109; 114; 115; 116; and 117. When length of CDR3-IMGT is 9 amino acids, it comprises the positions 105; 106; 107; 108; 109; 110; 112; 113; 114; 115; 116; and 117. If the CDR3-IMGT length is more than 13 amino acids, additional positions are created between positions 111 and 112 at the top of the CDR3-IMGT loop in the following order 112.1, 111.1, 112.2, 111.2, 112.3, 111.3, etc. Accordingly when the length of CDR3-IMGT is 15 amino acids, it comprises the additional positions 111.1 and 112.1.

All the single domain antibodies (hs2dAb) generated by the inventors are characterized by the same frameworks regions FR1-FR4 as described in Table A and comprises a CDR1-IMGT and a CDR2-IMGT having a length of 7 amino acids and a CDR3-IMGT having a length of 9, 12 or 15 amino acids as described in Table B.

TABLE A

| Framework region | Sequence |
|---|---|
| FR1 | VQLQASGGGFVQPGGSLRLSCAASG (SEQ ID NO: 1) |
| FR2 | MGWFRQAPGKEREFVSAISS (SEQ ID NO: 2) |
| FR3 | YYADSVKGRFTISRDNSKNTVYL QMNSLRAEDTATYYCA (SEQ ID NO: 3) |
| FR4 | YWGQGTQVTVSS (SEQ ID NO: 4) |

TABLE B

CDR-IMGT regions of the single domain antibodies (hs2dAb) generated by the inventors:

| hs2dAb | CDR1-IMGT | CDR2-IMGT | CDR3-IMGT |
|---|---|---|---|
| H12 | DGSRIYA (SEQ ID NO: 5) | WEQDWEH (SEQ ID NO: 6) | AFMTPH RNLTSM (SEQ ID NO: 7) |
| 4P75 | RYSAWDG (SEQ ID NO: 8) | SQHDLEE (SEQ ID NO: 9) | ATIRT GWAD (SEQ ID NO: 10) |
| 4SP1 | DTSDGYI (SEQ ID NO: 11) | EYNSQSE (SEQ ID NO: 12) | QSFNEVW KMPNKFPH (SEQ ID NO: 13) |
| 4SNP36 | TSWKDYT (SEQ ID NO: 14) | EGPGAQY (SEQ ID NO: 15) | YSSWQ PYVS (SEQ ID NO: 16) |
| 4SNP61 | FTSTSTV (SEQ ID NO: 17) | SAHTMDT (SEQ ID NO: 18) | YCAPAPM LGQMITQ PALP (SEQ ID NO: 19) |
| 5SP10 | RFWRRYT (SEQ ID NO: 20) | GTSDWT (SEQ ID NO: 21) | PPHFS GAAI (SEQ ID NO: 22) |
| 5SP11 | AGWRAEA (SEQ ID NO: 23) | SDGDHTI (SEQ ID NO: 24) | IMQTQMR RTSDYRF (SEQ ID NO: 25) |
| 5SP58 | DTFSDDV (SEQ ID NO: 26) | DWPTTQS (SEQ ID NO: 27) | YCAQANGD HSYPLWKY GNM (SEQ ID NO: 28) |
| 5SNP47 | RTSRFYS (SEQ ID NO: 29) | FNSDYFL (SEQ ID NO: 30) | AWWYRY TEGMTM (SEQ ID NO: 31) |
| 5SNP48 | TSWFTEV (SEQ ID NO: 32) | GLHDVGT (SEQ ID NO: 33) | ALDKWYTK AMDARKD (SEQ ID NO: 34) |
| 5SNP65 | ATYEGEA (SEQ ID NO: 35) | SYPSVIS (SEQ ID NO: 36) | YWVNHE GTIREI (SEQ ID NO: 37) |
| B6 | YGSTIET (SEQ ID NO: 38) | RAPGPSQ (SEQ ID NO: 39) | PINNRTMQ DSMFLWN (SEQ ID NO: 40) |
| B20 | TTSFWYT (SEQ ID NO: 41) | WRFNTTT (SEQ ID NO: 42) | 1PRYSLDA VPHRAST (SEQ ID NO: 43) |
| B15 | SYSRGET (SEQ ID NO: 44) | DTHNYET (SEQ ID NO: 45) | ASPQFHK IMKGSQV G (SEQ ID NO: 46) |

TABLE B-continued

CDR-IMGT regions of the single domain antibodies (hs2dAb) generated by the inventors:

| hs2dAb | CDR1-IMGT | CDR2-IMGT | CDR3-IMGT |
|---|---|---|---|
| B5 | ATSGGTV (SEQ ID NO: 47) | RSQTKAT (SEQ ID NO: 48) | PMEHEAL KQHPL (SEQ ID NO: 49) |
| B71 | DGSDGDV (SEQ ID NO: 50) | RYPGRSP (SEQ ID NO: 51) | ARWISRK WYTTPFQG (SEQ ID NO: 52) |
| E3 | STYETYA (SEQ ID NO: 53) | ASPTIEG (SEQ ID NO: 54) | TWSKM GISI (SEQ ID NO: 55) |
| A6 | DTWDQYV (SEQ ID NO: 56) | RSGTH GI (SEQ ID NO: 57) | PLTHQW MGRTFP (SEQ ID NO: 58) |
| G12 | RTSGWYA (SEQ ID NO: 59) | SRASSQE (SEQ ID NO: 60) | VWMKM GIEI (SEQ ID NO: 61) |
| NB61 | TTWFNEV (SEQ ID NO: 81) | GSTSWAE (SEQ ID NO: 82) | RMSFMR AGRTPM TPM (SEQ ID NO: 83) |
| 212B | DTWWSSA (SEQ ID NO: 84) | FYPTEYT (SEQ ID NO: 85) | WIAWGP WMRTSW (SEQ ID NO: 86) |
| 111B | GTSKQYG (SEQ ID NO: 87) | RQEGETI (SEQ ID NO: 88) | YRHVW PYPE (SEQ ID NO: 89) |
| 404F | RTSKNYA (SEQ ID NO: 90) | WTTNQDT (SEQ ID NO: 91) | IWDKR EISI (SEQ ID NO: 92) |

The antibodies (hs2dAb) are characterized by the sequences of Table C:

TABLE C sequences of the single domain antibodies (hs2dAb) generated by the inventors:

| hs2dAb | Sequence |
|---|---|
| H12 | VQLQASGGGFVQPGGSLRLSCAASGDGSRIYAMGWFRQAPGKEREFVSAISWEQDWEHYYADSVKGRFTISRDNSKNTVYLQMNSLRAEDTATYYCAAFMTPHRNLTSMYWGQGTQVTVSS (SEQ ID NO: 62) |
| 4P75 | VQLQASGGGFVQPGGSLRLSCAASGRYSAWDGMGWFRQAPGKEREFVSAISSQHDLEEYYADSVKGRTISRDNSKNTVYLQMNSLRAEDTATYYCAATIRTGWADYWGQGTQVTVSS (SEQ ID NO: 63) |
| 4SP1 | VQLQASGGGFVQPGGSLRLSCAASGDTSDGYIMGWFRQAPGKEREFVSAISEYNSQSEYYADSVKGRFTISRDNSKNTVYLQMNSLRAEDTATYYCAQSFNEVWKMPNKFPHYWGQGTQVTVSS (SEQ ID NO: 64) |
| 4SNP36 | VQLQASGGGFVQPGGSLRLSCAASGTSWKDYTMGWFRQAPGKEREFVSAISEGPGAQYYYADSVKGRFTISRDNSKNVYLQMNSLRAEDTATYYCAYSSWQPYVSYWGQGTQVTVSS (SEQ ID NO: 65) |
| 4SNP61 | VQLQASGGGFVQPGGSLRLSCAASGFTSTSTVMGWFRQAPGKEREFVSAISSAHTMDTYYADSVKGRFTISRDNSKNTVYLQMNSLRAEDTATYYCAPAPMLGQMITQPALPYWGQGTQVTVSS (SEQ ID NO: 66) |
| 5SP10 | VQLQASGGGFVQPGGSLRLSCAASGRFWRRYTMGWFRQAPGKEREFVSAISGTSDWTYYADSVKGRFTISRDNSKNTVYLQMNSLRAEDTATYYCAPPHFSGAAIYWGQGTQVTVSS (SEQ ID NO: 67) |
| 5SP11 | VQLQASGGGFVQPGGSLRLSCAASGAGWRAEAMGWFRQAPGKEREFVSAISSDGDHTIYYADSVKGRFTISRDNSKNTVYLQMNSLRAEDTATYYCAIMQTQMRRTSDYRFYWGQGTQVTVSS (SEQ ID NO: 68) |
| 5SP58 | VQLQASGGGFVQPGGSLRLSCAASGDTFSDDVMGWFRQAPGKEREFVSAISDWPTTQSYYADSVKGRFTISRDNSKNTVYLQMNSLRAEDTATYYCAQANGDHSYPLWKYGNMYWGQGTQVTVSS (SEQ ID NO: 69) |
| 5SNP47 | VQLQASGGGFVQPGGSLRLSCAASGRTSRFYSMGWFRQAPGKEREFVSAISFNSDYFLYYADSVKGRFTISRDNSKNTVYLQMNSLRAEDTATYYCAAWWYRYTEGMTMYWGQGTQVTVSS (SEQ ID NO: 70) |
| 5SNP48 | VQLQASGGGFVQPGGSLRLSCAASGTSWFTEVMGWFRQAPGKEREFVSAISGLHDVGTYYADSVKGRFTISRDNSKNTVYLQMNSLRAEDTATYYCAALDKWYTKAMDARKDYWGQGTQVTVSS (SEQ ID NO: 71) |
| 5SNP65 | VQLQASGGGFVQPGGSLRLSCAASGATYEGEAMGWFRQAPGKEREFVSAISSYPSVISYYADSVKGRFTISRDNSKNTVYLQMNSLRAEDTATYYCAYWVNHEGTIREIYWGQGTQVTVSS (SEQ ID NO: 72) |

TABLE C-continued sequences of the single domain antibodies (hs2dAb) generated by the inventors:

| hs2dAb | Sequence |
|---|---|
| B6 | VQLQASGGGFVQPGGSLRLSCA ASGYGSTIETMGWFRQAPGKER EFVSAISRAPGPSQYYADSVKG RFTISRDNSKNTVYLQMNSLRA EDTATYYCAPINNRTMQDSMFL WNYWGQGTQVTVSS (SEQ ID NO: 73) |
| B20 | VQLQASGGGFVQPGGSLRLSCA ASGTTSFWYTMGWFRQAPGKER EFVSAISWRFNTTTYYADSVKG RFTISRDNSKNTVYLQMNSLRA EDTATYYCAIPRYSLDAVPHRA STYWGQGTQVTVSS (SEQ ID NO: 74) |
| B15 | VQLQASGGGFVQPGGSLRLSCA ASGSYSRGETMGWFRQAPGKER EFVSAISDTHNYETYYADSVKG RFTISRDNSKNTVYLQMNSLRA EDTATYYCAASPQFHKIMKGSQ VGYWGQGTQVTVSS (SEQ ID NO: 75) |
| B5 | VQLQASGGGFVQPGGSLRLSCA ASGATSGGTVMGWFRQAPGKER EFVSAISRSQTKATYYADSVKG RFTISRDNSKNTVYLQMNSLRA EDTATYYCAPMEHEALKQHPLY WGQGTQVTVSS (SEQ ID NO: 76) |
| B71 | VQLQASGGGFVQPGGSLRLSCA ASGDGSDGDVMGWFRQAPGKER EFVSAISRYPGRSPYYADSVKG RFTISRDNSKNTVYLQMNSLRA EDTATYYCAARWISRKWYTTPF QGYWGQGTQVTVSS (SEQ ID NO: 77) |
| E3 | VQLQASGGGFVQPGGSLRLSCA ASGSTYETYAMGWFRQAPGKER EFVSAISASPTIEGYYADSVKG RFTISRDNSKNTVYLQMNSLRA EDTATYYCATWSKMGISIYWGQ GTQVTVSS (SEQ ID NO: 78) |
| A6 | VQLQASGGGFVQPGGSLRLSCA ASGDTWDQYVMGWFRQAPGKER EFVSAISRSGTHGIYYADSVKG RFTISRDNSKNTVYLQMNSLRA EDTATYYCAPLTHQWMGRTFPY WGQGTQVTVSS (SEQ ID NO: 79) |
| G12 | VQLQASGGGFVQPGGSLRLSCA ASGRTSGWYAMGWFRQAPGKER EFVSAISSRASSQEYYADSVKG RFTISRDNSKNTVYLQMNSLRA EDTATYYCAVWMKMGIEIYWGQ GTQVTVSS (SEQ ID NO: 80) |
| NB61 | VQLQASGGGFVQPGGSLRLSCA ASGTTWFNEVMGWFRQAPGKER EFVSAISGSTSWAEYYADSVKG RFTISRDNSKNTVYLQMNSLRA EDTATYYCARMSFMRAGRTPMT PMYWGQGTQVTVSS (SEQ ID NO: 93) |
| 212B | VQLQASGGGFVQPGGSLRLSCA ASGDTWWSSAMGWFRQAPGKER EFVSAISFYPTEYTYYADSVKG RFTISRDNSKNTVYLQMNSLRA EDTATYYCAWIAWGPWMRTSWY WGQGTQVTVSS (SEQ ID NO: 94) |
| 111B | VQLQASGGGFVQPGGSLRLSCA ASGGTSKQYGMGWFRQAPGKER EFVSAISRQEGETIYYADSVKG RFTISRDNSKNTVYLQMNSLRA EDTATYYCAYRHVWPYPEYWGQ GTQVTVSS (SEQ ID NO: 95) |
| 404F | VQLQASGGGFVQPGGSLRLSCA ASGRTSKNYAMGWFRQAPGKER EFVSAISWTTNQDTYYADSVKG RFTISRDNSKNTVYLQMNSLRA EDTATYYCAIWDKREISIYWGQ GTQVTVSS (SEQ ID NO: 96) |

A first object of the present invention relates to a single domain antibody wherein the amino acid sequences of CDR1-IMGT, CDR2-IMGT and CDR3-IMGT have at least 90% of identity with the amino acid sequences of the CDR1-IMGT, CDR2-IMGT and CDR3-IMGT of the H12, 4P75, 4SP1, 4SNP36, 4SNP61, 5SP10, 5SP11, 5SP58, 5SNP47, 5SNP48, 5SNP65, B6, B20, B15, B5, B71, E3, A6, G12, NB61, 212B, 111B or 404F (hs2dAb) single domain antibody.

According to the invention a first amino acid sequence having at least 90% of identity with a second amino acid sequence means that the first sequence has 90; 91; 92; 93; 94; 95; 96; 97; 98; 99 or 100% of identity with the second amino acid sequence. Amino acid sequence identity is typically determined using a suitable sequence alignment algorithm and default parameters, such as BLAST P (Karlin and Altschul, 1990).

In some embodiments the single domain antibody of the present invention comprises the CDR1-IMGT, CDR2-IMGT and CDR3-IMGT of the H12, 4P75, 4SP1, 4SNP36, 4SNP61, 5SP10, 5SP11, 5SP58, 5SNP47, 5SNP48, 5SNP65, B6, B20, B15, B5, B71, E3, A6, G12, NB61, 212B, 111B or 404F (hs2dAb) single domain antibody.

In some embodiments, the single domain antibody of the present invention comprises a framework region FR1 having at least 90% of identity with SEQ ID NO:1.

In some embodiments, the single domain antibody of the present invention comprises a framework region FR2 having at least 90% of identity with SEQ ID NO:2.

In some embodiments, the single domain antibody of the present invention comprises a framework region FR3 having at least 90% of identity with SEQ ID NO:3.

In some embodiments, the single domain antibody of the present invention comprises a framework region FR4 having at least 90% of identity with SEQ ID NO:4.

In some embodiments the single domain antibody of the present invention comprises the framework regions FR1-FR4 having at least 90% of identity with SEQ ID NO:1-4 respectively.

In some embodiments, the single domain antibody of the present invention comprises an amino acid sequence having at least 70% of identity with the amino acid sequence represented by SEQ ID NO:62-80 and SEQ ID NO: 93-96.

According to the invention a first amino acid sequence having at least 70% of identity with a second amino acid sequence means that the first sequence has 70; 71; 72; 73; 74; 75; 76; 77; 78; 79; 80; 81; 82; 83; 84; 85; 86; 87; 88; 89; 90; 91; 92; 93; 94; 95; 96; 97; 98; or 99% of identity with the second amino acid sequence.

In some embodiments, the single domain antibody of the present invention comprises an amino acid sequence having at least 90% of identity with the amino acid sequence represented by SEQ ID NO:62-80 and SEQ ID NO: 93-96.

In some embodiment, the single domain antibody of the present invention comprises an amino acid sequence selected from the group consisting of the amino acid sequences represented by SEQ ID NO:62-80 and SEQ ID NO: 93-96.

In some embodiment, the single domain antibody of the present invention is fused to a heterologous polypeptide to form fusion protein. As used herein, a "fusion protein" comprises all or part (typically biologically active) of a single domain antibody of the present invention operably linked to a heterologous polypeptide (i.e., a polypeptide other than the same single domain antibody). Within the fusion protein, the term "operably linked" is intended to indicate that the polypeptide of the invention and the heterologous polypeptide are fused in-frame to each other. The heterologous polypeptide can be fused to the N-terminus or C-terminus of the single domain antibody of the invention. In some embodiment, the heterologous polypeptide is fused to the C-terminal end of the single domain antibody of the present invention.

In some embodiments, the single domain antibody of the present invention and the heterologous polypeptide are fused to each other directly (i.e. without use of a linker) or via a linker. The linker is typically a linker peptide and will, according to the invention, be selected so as to allow binding of the single domain antibody to the heterologous polypeptide. Suitable linkers will be clear to the skilled person based on the disclosure herein, optionally after some limited degree of routine experimentation. Suitable linkers are described herein and may—for example and without limitation—comprise an amino acid sequence, which amino acid sequence preferably has a length of 2 or more amino acids. Typically, the linker has 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. However, the upper limit is not critical but is chosen for reasons of convenience regarding e.g. biopharmaceutical production of such fusion proteins. The linker sequence may be a naturally occurring sequence or a non-naturally occurring sequence. If used for therapeutical purposes, the linker is preferably non-immunogenic in the subject to which the fusion protein of the present invention is administered. One useful group of linker sequences are linkers derived from the hinge region of heavy chain antibodies as described in WO 96/34103 and WO 94/04678. Other examples are poly-alanine linker sequences such as Ala-Ala-Ala. Further preferred examples of linker sequences are Gly/Ser linkers of different length including (gly4ser)3, (gly4ser)4, (gly4ser), (gly3ser), gly3, and (gly3 ser2)3.

In some embodiments, the single domain antibody of the invention is fused to an immunoglobulin domain. For example the fusion protein of the present invention may comprise a single domain antibody of the invention that is fused to an Fc portion (such as a human Fc). Said Fc portion may be useful for increasing the half-life and even the production of the single domain antibody of the invention. For example the Fc portion can bind to serum proteins and thus increases the half-life on the single domain antibody. In some embodiments, the at least one single domain antibody may also be fused to one or more (typically human) CH1, and/or CH2 and/or CH3 domains, optionally via a linker sequence. For instance, a single domain antibody fused to a suitable CH1 domain could for example be used—together with suitable light chains—to generate antibody fragments/structures analogous to conventional Fab fragments or F(ab')2 fragments, but in which one or (in case of an F(ab')2 fragment) one or both of the conventional VH domains have been replaced by a single domain antibody of the invention. In some embodiments, one or more single domain antibodies of the invention may be fused to one or more constant domains (for example, 2 or 3 constant domains that can be used as part of/to form an Fc portion), to an Fc portion and/or to one or more antibody parts, fragments or domains that confer one or more effector functions and/or may confer the ability to bind to one or more Fc receptors. For example, for this purpose, and without being limited thereto, the one or more further amino acid sequences may comprise one or more CH2 and/or CH3 domains of an antibody, such as from a heavy chain antibody and more typically from a conventional human chain antibody; and/or may form and Fc region, for example from IgG (e.g. from IgG1, IgG2, IgG3 or IgG4), from IgE or from another human Ig such as IgA, IgD or IgM. For example, WO 94/04678 describes heavy chain antibodies comprising a Camelid VHH domain or a humanized derivative thereof (i.e. a single domain antibody), in which the Camelidae CH2 and/or CH3 domain have been replaced by human CH2 and CH3 domains, so as to provide an immunoglobulin that consists of 2 heavy chains each comprising a single domain antibody and human CH2 and CH3 domains (but no CHI domain), which immunoglobulin has the effector function provided by the CH2 and CH3 domains and which immunoglobulin can function without the presence of any light chains.

In some embodiments, the heterologous polypeptide is a single domain antibody. Accordingly, in some embodiments, the fusion protein of the present invention is a biparatopic polypeptide. As used herein, the term "biparatopic" polypeptide means a polypeptide comprising a first single domain antibody and a second single domain antibody as herein defined, wherein these two single domain antibodies are capable of binding to two different epitopes of one antigen (i.e. Rho GTPase). The biparatopic polypeptides according to the invention are composed of single domain antibodies which have different epitope specificities, and do not contain mutually complementary variable domain pairs which bind to the same epitope. They do therefore not compete with each other for binding to Rho GTPase.

In some embodiments, the heterologous polypeptide is a carrier polypeptide. Suitable carriers are well known in the art, and include, e.g., thyroglobulin, albumins such as human serum albumin, tetanus toxoid; Diphtheria toxoid; polyamino acids such as poly(D-lysine:D-glutamic acid); VP6 polypeptides of rotaviruses; influenza virus hemagglutinin, influenza virus nucleoprotein; hepatitis B virus core protein, hepatitis B virus surface antigen; purified protein derivative (PPD) of tuberculin from *Mycobacterium tuberculosis*; inactivated *Pseudomonas aeruginosa* exotoxin A (toxin A); Keyhole Limpet Hemocyanin (KLH); filamentous hemagglutinin (FHA) of *Bordetella pertussis*; T helper cell (Th) epitopes of tetanus toxoid (TT) and *Bacillus* Calmette-Guerin (BCG) cell wall; recombinant 10 kDa, 19 kDa and 30-32 kDa proteins from *M. leprae* or from *M. tuberculosis*, or any combination of these proteins; and the like.

In some embodiments, the heterologous polypeptide is a fluorescent polypeptide. Suitable fluorescent polypeptides include, but are not limited to, a green fluorescent protein (GFP), including, but not limited to, a "humanized" version of a GFP, e.g., wherein codons of the naturally-occurring nucleotide sequence are changed to more closely match human codon bias; a GFP derived from *Aequoria victoria* or a derivative thereof, e.g., a "humanized" derivative such as Enhanced GFP, which are available commercially, e.g., from Clontech, Inc.; a GFP from another species such as *Renilla reniformis, Renilla mulleri*, or Ptilosarcus guernyi, as described in, e.g., WO 99/49019 and Peelle et al. (2001) J. Protein Chem. 20:507-519; "humanized" recombinant GFP (hrGFP) (Stratagene); any of a variety of fluorescent and colored proteins from Anthozoan species, as described in, e.g., Matz et al. (1999) Nature Biotechnol. 17:969-973; and the like.

In some embodiments, the heterologous polypeptide is an enzyme. Typically, said enzyme may be selected from the group consisting of β-galactosidase, alkaline phosphatase, luciferase, and horse radish peroxidise). Where the heterologous polypeptide is an enzyme that yields a detectable product, the product can be detected using an appropriate means, e.g., β-galactosidase can, depending on the substrate, yield colored product, which is detected spectrophotometrically, or a fluorescent product; luciferase can yield a luminescent product detectable with a luminometer; etc.

In some embodiments, the heterologous polypeptide is a polypeptide that facilitates purification or isolation of the fusion protein, e.g., metal ion binding polypeptides such as 6H is tags (e.g., acetylated Tat/6His), or glutathione-S-transferase.

In some embodiments, the heterologous polypeptide is a cell-penetrating peptide. The term "cell-penetrating peptides" is well known in the art and refers to cell permeable sequences or membranous penetrating sequences such as penetratin, TAT mitochondrial penetrating sequence and compounds described in Bechara and Sagan, 2013; Jones and Sayers, 2012; Khafagy el and Morishita, 2012; and Malhi and Murthy, 2012. In a particular embodiment, the heterologous polypeptide is the Transactivator of Transcription (TAT) cell penetrating sequence originally derived from the cell-penetrating HIV tat peptide.

In some embodiments, the heterologous polypeptide is a domain of an ubiquitin ligase, such as E3 ubiquitin ligase. Examples of various E3 ubiquitin ligase domains include RING, HECT, U-box, RIBRR, F-box domain, DCAF domain, DDS2, HIF-mimetic peptides, IkB-mimetic sequences, BTB domain, or combination thereof. These E3 ligase domains facilitate ubiquitination, and when fused with the single domain antibody of the present allows for the degradation of the antigen-antibody complex. Any E3 ligase domains including E2 binding domains known or later discovered or developed can be used. Recombinant E3 ligase domains can be used. In some embodiment, the heterologous polypeptide is a F-box domain. The F-box domain is typically a protein motif of approximately 50 amino acids. The F-box domain tethers the F-box protein to other components of the SCF complex by binding the core SCF component, Skp1.

In some embodiments, the heterologous polypeptide is a switchable domain, which can be activated by a small molecule or by photoactivation. Examples of small molecule switchable system include hormone ligand binding domain such as ERalpha LBD, Auxin AID system, HaloTag2 derivative system HyT or HALTS, FKB-FRB rapamycin or shield1 systems. Examples of photoactivation systems include Lov2 domain, PhyB-PIF, Cry2, UVR8, or Dronpa. These switchable systems are typically used for a precise spatial or temporal control of protein functions by conformational changed or relocalisation.

The single domain antibody of the present invention (fused or not to the heterologous polypeptide) is produced by any technique known in the art, such as, without limitation, any chemical, biological, genetic or enzymatic technique, either alone or in combination. For example, knowing the amino acid sequence of the desired sequence, one skilled in the art can readily produce said single domain antibody (fused or not to the heterologous polypeptide), by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, the single domain antibody of the present invention (fused or not to the heterologous polypeptide) can be synthesized by recombinant DNA techniques well-known in the art. For example, the single domain of the present invention (fused or not to the heterologous polypeptide) can be obtained as DNA expression products after incorporation of DNA sequences encoding the single domain antibody (fused or not to the heterologous polypeptide) into expression vectors and introduction of such vectors into suitable eukaryotic or prokaryotic hosts that will express the desired single domain antibody, from which they can be later isolated using well-known techniques. A variety of expression vector/host systems may be utilized to contain and express the single domain antibody of the present invention (fused or not to the heterologous polypeptide). These include but are not limited to microorganisms such as bacteria transformed with recombinant bacteriophage, plasmid or cosmid DNA expression vectors; yeast transformed with yeast expression vectors (Giga-Hama et al., 1999); insect cell systems infected with virus expression vectors (e.g., baculovirus, see Ghosh et al., 2002); plant cell systems transfected with virus expression vectors (e.g., cauliflower mosaic virus, CaMV; tobacco mosaic virus, TMV) or transformed with bacterial expression vectors (e.g., Ti or pBR322 plasmid; see e.g., Babe et al., 2000); or animal cell systems. Those of skill in the art are aware of various techniques for optimizing mammalian expression of proteins, see e.g., Kaufman, 2000; Colosimo et al., 2000. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein. In the recombinant production of the single domain antibody of the present invention (fused or not to the heterologous polypeptide), it would be necessary to employ vectors comprising polynucleotide molecules for encoding said single domain antibody. Methods of preparing such vectors as well as producing host cells transformed with such vectors are well known to those skilled in the art. The polynucleotide molecules used in such an endeavour may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation. The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed. The choice of a suitable expression vector for expression of single domain antibody of the present invention will of course depend upon the specific host cell to be used, and is within the skill of the ordinary artisan. Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. Typically, the nucleotide sequences are operably linked when the regulatory sequence functionally relates to the DNA encoding the protein of interest (e.g., a single domain antibody). Thus, a promoter nucleotide sequence is operably linked to a given DNA sequence if the promoter nucleotide sequence directs the transcription of the sequence. They may then, if necessary, be purified by conventional procedures, known in themselves to those skilled in the art, for example by fractional precipitation, in particular ammonium sulphate precipitation, electrophoresis, gel filtration, affinity chromatography, etc. In particular, conventional methods for preparing and purifying recombinant proteins may be used for producing the proteins in accordance with the invention.

A further object of the present invention relates to a nucleic acid molecule which encodes for a single domain antibody of the present invention (fused or not to the heterologous polypeptide).

As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid molecule of the present invention is included in a suitable vector, such as a plasmid, cosmid, episome, artificial chromosome, phage or a viral vector. So, a further object of the invention relates to a vector comprising a nucleic acid encoding for a single domain antibody of the invention (fused or not to the heterologous polypeptide). Typically, the vector is a viral vector which is an adeno-associated virus (AAV), a retrovirus, bovine papilloma virus, an adenovirus vector, a lentiviral vector, a vaccinia virus, a polyoma virus, or an infective virus. In some embodiments, the vector is an AAV vector. As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

A further object of the present invention relates to a host cell transformed with the nucleic acid molecule of the present invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". For instance, as disclosed above, for expressing and producing the single domain antibody of the present invention, prokaryotic cells and, in particular *E. coli* cells, will be chosen. Actually, according to the invention, it is not mandatory to produce the single domain antibodys of the present invention in a eukaryotic context that will favour post-translational modifications (e.g. glycosylation). Typically, the host cell may be suitable for producing the single domain antibody of the present invention (fused or not to the heterologous polypeptide) as described above. In some cases, the host cell is used as a research tool, to study e.g. the impact of the Rho GTPase activation or inactivation (e.g. functional knockdown) in a cell of interest as described in the EXAMPLE. In some embodiments, the host cells is isolated from a mammalian subject who is selected from a group consisting of: a human, a horse, a dog, a cat, a mouse, a rat, a cow and a sheep. In some embodiments, the host cell is a human cell. In some embodiments, the host cell is a cell in culture. The cells may be obtained directly from a mammal (preferably human), or from a commercial source, or from tissue, or in the form for instance of cultured cells, prepared on site or purchased from a commercial cell source and the like. The cells may come from any organ including but not limited to the blood or lymph system, from muscles, any organ, gland, the skin, brain, lung . . . In some embodiments, the cells are selected from the group consisting of epithelial cells, neural cells, epidermal cells, keratinocytes, hematopoietic cells, melanocytes, chondrocytes, hepatocytes, B-cells, T-cells, erythrocytes, macrophages, monocytes, fibroblasts, muscle cells, vascular smooth muscle cells, hepatocytes, splenocytes, pancreatic β cells . . . . In some embodiments, the host cell is a cancer cell. Typically, the cancer cells are isolated from a cancer selected from the group consisting of breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiment, the host cells is a stem cell. As used herein, the term "stem cell" refers to an undifferentiated cell that can be induced to proliferate. The stem cell is capable of self-maintenance or self-renewal, meaning that with each cell division, one daughter cell will also be a stem cell. Stem cells can be obtained from embryonic, post-natal, juvenile, or adult tissue. Stem cells can be pluripotent or multipotent. The term "progenitor cell," as used herein, refers to an undifferentiated cell derived from a stem cell, and is not itself a stem cell. Some progenitor cells can produce progeny that are capable of differentiating into more than one cell type. Stem cells include pluripotent stem cells, which can form cells of any of the body's tissue lineages: mesoderm, endoderm and ectoderm. Therefore, for example, stem cells can be selected from a human embryonic stem (ES) cell; a human inner cell mass (ICM)/epiblast cell; a human primitive ectoderm cell, a human primitive endoderm cell; a human primitive mesoderm cell; and a human primordial germ (EG) cell. Stem cells also include multipotent stem cells, which can form multiple cell lineages that constitute an entire tissue or tissues, such as but not limited to hematopoietic stem cells or neural precursor cells. Stem cells also include totipotent stem cells, which can form an entire organism. In some embodiment, the stem cell is a mesenchymal stem cell. The term "mesenchymal stem cell" or "MSC" is used interchangeably for adult cells which are not terminally differentiated, which can divide to yield cells that are either stem cells, or which, irreversibly differentiate to give rise to cells of a mesenchymal cell lineage, e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines.

In some embodiments, the stem cell is a partially differentiated or differentiating cell. In some embodiments, the stem cell is an induced pluripotent stem cell (iPSC), which has been reprogrammed or de-differentiated. Stem cells can be obtained from embryonic, fetal or adult tissues.

The single domain antibody of the present invention (fused or not to the heterologous polypeptide) may be used in the research and diagnostic field. For instance, the single domain antibody of the invention is thus particularly suitable for detecting the present of an activated form of a Rho GTPase, said detection may find usefulness for research or diagnostic purpose.

Thus, a further aspect of the present invention, there is provided a method of detecting the present of a least one activated form of a Rho GTPase (e.g. RhoA, RhoB, and/or RhoC) comprising the steps of i) a) obtaining a sample from a subject, ii) contacting, in vitro, the sample with a single domain antibody of the present invention (fused or not to the heterologous polypeptide), iii) detecting the binding of said single domain antibody to said sample, and iv) comparing the binding detected in step (iii) with a standard, wherein a difference in binding relative to said sample indicated the presence of the activated form of the Rho GTPase. Typically, the detection is performed with any suitable means such as a microscope or an automated analysis system.

As used herein the term "sample" encompasses a variety of sample types obtained from a subject and can be used in a diagnostic or research assay. Biological samples include but are not limited to blood and other liquid samples of biological origin, solid tissue samples such as a biopsy specimen or tissue cultures or cells derived therefrom, and the progeny thereof. In some embodiments, the sample is a tumor tissue sample. The term "tumor sample" means any tissue sample derived from the tumor of the subject. The tissue sample is obtained for the purpose of the in vitro evaluation and typically results from biopsy performed in a tumor of the subject. The sample can be fresh, frozen, or embedded (e.g., FFPE biopsy).

Accordingly, in some embodiments, the single domain antibody of the present invention (fused or not to the heterologous polypeptide) is conjugated with a detectable label. Suitable detectable labels include, for example, a radioisotope, a fluorescent label, a chemiluminescent label, an enzyme label, a bio luminescent label or colloidal gold. Methods of making and detecting such detectably-labeled immunoconjugates are well-known to those of ordinary skill in the art, and are described in more detail below. For instance, the detectable label can be a radioisotope that is detected by autoradiography. Isotopes that are particularly useful for the purpose of the present invention are 3H, 125I, 131I, 35S and 14C. The single domain antibody of the present invention (fused or not to the heterologous polypeptide) can also be labeled with a fluorescent compound. The presence of a fluorescently-labeled single domain antibody of the present invention is determined by exposing the immuno conjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine and Alexa Fluor dyes. Alternatively, the single domain antibody of the present invention can be detectably labeled by coupling said single domain antibody to a chemiluminescent compound. The presence of the chemiluminescent-tagged immuno conjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester. Similarly, a bio luminescent compound can be used to label the single domain antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin. Typically, when the single domain antibody is fused to a fluorescent polypeptide as described above, the presence of the fusion protein can be detected with any means well known in the art such as a microscope or microscope or automated analysis system. Typically, when the single domain antibody is fused to an enzyme then, the fusion protein is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase. Those of skill in the art will know of other suitable labels which can be employed in accordance with the present invention. The binding of marker moieties to anti-the single domain antibody of the present invention is accomplished using standard techniques known to the art. Typical methodology in this regard is described by Kennedy et al., Clin. Chim. Acta 70: 1, 1976; Schurs et al., Clin. Chim. Acta 81: 1, 1977; Shih et al., Int'U. Cancer 46: 1101, 1990; Stein et al, Cancer Res. 50: 1330, 1990; and Coligan, supra. Moreover, the convenience and versatility of immunochemical detection can be enhanced by using single domain antibodies of the present invention (fused or not to the heterologous polypeptide) that have been conjugated with avidin, streptavidin, and biotin. {See, e.g., Wilchek et al. (eds.), "Avidin-Biotin Technology", Methods In Enzymology (Vol. 184) (Academic Press 1990); Bayer et al., "Immunochemical Applications of Avidin-Biotin Technology," in Methods In Molecular Biology (Vol. 10) 149-162 (Manson, ed., The Humana Press, Inc. 1992).) In some embodiments, the presence of the single domain antibody (fused or not to the heterologous polypeptide) is detected with a secondary antibody that is specific for the single antibody of the present invention (fused or not to the heterologous polypeptide). Typically said secondary is labeled by same methods as described above. For instance when the single domain antibody of the present invention is fused to a tag (e.g. histidine tag) the secondary antibody is specific for said tag. Methods for performing immunoassays are well-established. {See, e.g., Cook and Self, "Monoclonal Antibodies in Diagnostic Immunoassays", in Monoclonal Antibodies: Production, Engineering, and Clinical Application 180-208 (Ritter and Ladyman, eds., Cambridge University Press 1995); Perry, "The Role of Monoclonal Antibodies in the Advancement of Immunoassay Technology", in Monoclonal Antibodies: Principles and Applications 107-120 (Birch and Lennox, eds., Wiley-Liss, Inc. 1995); Diamandis, Immunoassay (Academic Press, Inc. 1996)).

The single domain antibody of the present invention (fused or not to the heterologous polypeptide) and nucleic acid molecules encoding thereof can be used as medicament. In particular, the nucleic acid molecules of the present invention (inserted or not into a vector) are particularly suitable for gene therapy.

In some embodiments, the single domain antibody and nucleic acid molecules of the present invention (inserted or not into a vector) are particularly suitable for the treatment of cancer. As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, oesophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; para-granuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Accordingly a further object of the present invention relates to a method for treating cancer in a subject in need thereof comprising administering the subject with a therapeutically effective amount of a single domain antibody of the present invention (fused or not to the heterologous polypeptide) or a nucleic acid molecule of the present invention which is inserted or not in to a vector as above described.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By a "therapeutically effective amount" is meant a sufficient amount of the single domain antibody or the nucleic acid molecule of the present invention thereof for the treatment of the disease at a reasonable benefit/risk ratio applicable to any medical treatment. It will be understood that the total daily usage of the active agent will be decided by the attending physician within the scope of sound medical judgment. The specific therapeutically effective dose level for any particular subject will depend upon a variety of factors including the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well known within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

According to the invention, the single domain antibody (fused or not to the heterologous polypeptide) or the nucleic acid molecule (inserted or not into a vector) of the present invention is administered to the subject in the form of a pharmaceutical composition. Typically, the single domain antibody or the nucleic acid molecule (inserted or not into a vector) of the present invention may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The single domain antibody or the nucleic acid molecule (inserted or not into a vector) of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the typical methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIGS. 1A-1C: The H12 hs2dAb is selective for Rho in its active conformation. (A) H12 is a conformational hs2dAb binding only to the GTP bound, activated state of RhoA GTPase. ELISA revealing recombinant GST-RhoA wild type loaded with either 100 μM GTP gamma S (Black)) or 1 mM GDP (White), or a purified GST fusion of a RhoA constitutively active mutant Q63L (Check). (B) A CBD tagged H12 pull down from HeLa cell extract loaded with 100 μM GTP gamma S (GTP) or with 1 mM GDP as inputs. Western blot reveals RhoA at similar level in 5% of both input but only on the GTP loaded extract in the CBD-H12 pull down. D5 anti tubulin was a used as negative control and the standard GST-RBD (Rho binding domain of Rhotekin) as a positive control of active Rho pull down. (C) immunofluorescence on HeLa cells overexpressing GFP-RhoAT19N inactive mutant or GFPRhoAQ63L. H12 staining detected using a myc tag antibody revealed only cells overexpressing the constitutively active mutant with a pattern similar to the GFP fluorescence.

FIG. 2: The H12 hs2dAb is able to perturb endogenous Rho activity when expressed in the cytosol. HeLa cells transfected with a control non relevant hs2dAb or the clone H12 anti Rho-GTP expressed as GFP fusion. Cells were fixed 20 h hours post transfection and stained with DAPI and Alexa 594 phalloidin to label actin stress fibers.

FIGS. 3A-3E: Characterization of selected F-Ib. (A) mCherry fluorescence quantification by flow cytometry in Hm and HmB cell lines. After 48 h of F-Ib transfection in the Hm and the HmB cell lines, the mCherry fluorescence was quantified in the transfected subpopulation and in the non transfected subpopulation for each F-Ib. The ratio of each median of fluorescence (transfected versus non transfected population) gives a percentage of mCherry fluorescence intensity for one F-Ib. (B) Fbox domain is responsible of RhoB degradation in HmB cell line. F-hs2dAb and hs2dAb were transfected in HmB cell line. The median of mCherry fluorescence was determined by flow cytometry as in (A). A decrease of mCherry fluorescence is only observed with the F-Ib whereas the hs2dAb alone are not able to induce such decay. (C) Degradation in HmB cell line is proteasome dependent. HmB cells were transfected with F-Ib and treated 36 h with 1 μM of MG132 (a proteasome inhibitor) or DMSO. MG132 treatment restores the fluorescence level nearly to the control level. Medians of fluorescence are normalized to the NR control. (D) F-H12 and F-B5 degrade Rac1 mutant. After 48 h of F-Ib transfection, the mCherry fluorescence was quantified by flow cytometry in Hm, HmB and H2B-mCherry-Rac1L63 cell lines as describe in (A) and median of fluorescence for each cell line was normalized to the NR control. F-H12 and F-B5 induce a significant decrease of mCherry fluorescence in Rac1L63 cell line compared to the other F-Ib. (E) All RhoB positive F-Ib are conformational sensitive, selective towards the active mutant RhoBL63. As describe above, the mCherry fluorescence was quantified by flow cytometry after F-Ib transfection in Hm, HmB and H2B-mCherry-RhoBN19 cell lines and median of fluorescence for each cell line was normalized to the NR control. No significant decrease in mCherry fluorescence was observed in RhoBN19 cell line compared to the control cell line Hm for each F-Ib.

FIGS. 4A-4E: Endogenous RhoB cellular activation knockdown. (A) Hela S3 cells were transfected 48 h with F-Ib plasmids. A GST-RBD pulldown was performed for each F-Ib to control Rho-GTP level (lines RhoB-GTP, RhoA-GTP and RhoC-GTP) and the total level of Rho proteins was revealed by loading 2% of input (lines total RhoB, total RhoA and total RhoC). F-Ib production is shown with myc tag revelation and tubulin is the loading control. (B) Quantification of three independent GST-RBD pulldown experiments. F-B6 seems to degrade more selectively RhoB-GTP than RhoA or RhoC. F-H12 and F-B15 are pan Rho binders. Relative activity was calculated as the ratio between GTP level to input level normalized to tubulin. Normalized means±SEM are shown. (C) RhoB activation kinetic after an EGF treatment. HeLa S3 cells were transfected with F-NR control 48 h including 24 h of serum starvation. At 48 h of transfection, cells were treated at an EGF concentration of 50 ng.mL-1 for indicated times. A GST-RBD pulldown was performed to monitor the Rho-GTP induction following this treatment. RhoB is activated within 5 min until 30 min and a second wave of activation is shown at 120 min. RhoA and RhoC are activated only between 5 and 30 min with a maximum at 5 min. (C, D, E) After 15 min of EGF treatment and 48 h of cells transfection by F-Ib, RhoB-GTP (C), RhoA-GTP (D) and RhoC-GTP (E) levels were checked. F-H12 and F-B6 are able to inhibit RhoB activation following an EGF treatment compared to the negative control. F-H12 inhibits partially RhoA activation (50%) and nearly decreases RhoC-GTP level to the basal level (without treatment) under EGF treatment whereas F-B6 has no inhibitory effect after EGF treatment on these two RhoGTPases activation. Quantification is shown with normalized means±SEM.

EXAMPLES

Example 1: Selection of Conformation-Sensitive Antibodies

One of the main advantages of full in vitro immunization using display technologies is the control of antigen conformation and concentration in order to drive selection towards the desired outcome. For example, selection schemes can be devised to improve the recovery of high affinity binders endowed with low off-rate kinetics, to target specific epitopes, or to identify conformation sensitive-binders. Recombinant antibody fragment library screening have for example provided several binders targeting selectively the active conformation of small GTPase. We hypothesized that our synthetic library (described in PCT/EP2014/073713) had enough diversity and functionality to enable the identification of selective conformational binders. We carried out subtractive panning to select conformation-specific antibodies directed against small GTPases from the Rho subfamily. Small GTPases are molecular switch that cycle between an inactive and an active state when bound to GDP or GTP nucleotides respectively. Mutant of small GTPases can be designed that adopt stably an active or inactive conformation. A constitutively active mutant (e.g. RhoA Q63L, RhoB Q63L or RhoC Q63L) was expressed in HEK293 as bait then freshly pulled down for panning to preserve its native conformation. To enrich in phage specific for GTP-bound RhoA, a depletion step was introduced from the second round of panning using GDP-bound RhoA proteins, to remove generic binders before selecting against the active mutant. After four rounds of selection, clones were analyzed using phage ELISA against either the Rho GTPase bound to GTPγS (a non-hydrolysable analogue of GTP)-loaded Rho GTPase or GDP-loaded Rho GTPase. The basic features of the selected single domain antibodies are depicted in Table 1:

TABLE 1 basic features of the selected single domain anti bodies:

| Name | ELISA | IF | IP | IB | (2SHA) | Kon ($10^6$ $M^{-1} \cdot sec^{-1}$) | Koff ($10^{-3}$ $sec^{-1}$) | Kd (nM) |
|---|---|---|---|---|---|---|---|---|
| H12 | X | X | X | X | RhoA Q63L | 4.81+5 | 1.28−4 | 2.65−10 = 0.265 nM |
|  |  |  |  |  | RhoB Q63L | 2.24+5 | 3.59−4 | 1.57−9 = 1.57 nM |
|  |  |  |  |  | RhoC Q63L | 1.12+6 | 5.41−5 | 4.79−11 = 0.0479 nM |
|  |  |  |  |  | RhoA T19N | négatif | négatif | négatif |
|  |  |  |  |  | Rac Q61L | 7.53+5 | 2.55−4 | 3.3−10 = 0.33 nM |
| 4P75 | X | X | ND | ND | RhoA Q63L | ND | ND | ND |
|  |  |  |  |  | RhoB Q63L | ND | ND | ND |
|  |  |  |  |  | RhoC Q63L | ND | ND | ND |
|  |  |  |  |  | RhoA T19N | ND | ND | ND |
|  |  |  |  |  | Rac Q61L | ND | ND | ND |
| 4SP1 | X | X | X | X | RhoA Q63L | ND | ND | ND |
|  |  |  |  |  | RhoB Q63L | ND | ND | ND |
|  |  |  |  |  | RhoC Q63L | ND | ND | ND |
|  |  |  |  |  | RhoA T19N | ND | ND | ND |
|  |  |  |  |  | Rac Q61L | ND | ND | ND |
| 4SNP36 | X | 0 | X | X | RhoA Q63L | 1.76+6 | 5.22−4 | 2.96−10 = 0.296 nM |
|  |  |  |  |  | RhoB Q63L | 2.99+6 | 8.34−4 | 2.78−10 = 0.278 nM |
|  |  |  |  |  | RhoC Q63L | 6.52+6 | 5.42−4 | 8.31−11 = 0.0831 nM |
|  |  |  |  |  | RhoA T19N | ND | ND | ND |
|  |  |  |  |  | Rac Q61L | ND | ND | ND |
| 4SNP61 | X | 0 | X | X | RhoA Q63L | 1.10+6 | 0.0013 | 1.21−9 = 1.21 nM |
|  |  |  |  |  | RhoB Q63L | 7.22+5 | 0.0033 | 4.68−9 = 4.68 nM |
|  |  |  |  |  | RhoC Q63L | 8.75+5 | 0.0046 | 5.30−9 = 5.30 nM |
|  |  |  |  |  | RhoA T19N | ND | ND | ND |
|  |  |  |  |  | Rac Q61L | ND | ND | ND |
| 5SP10 | X | 0 | X | X | RhoA Q63L | ND | ND | ND |
|  |  |  |  |  | RhoB Q63L | ND | ND | ND |
|  |  |  |  |  | RhoC Q63L | ND | ND | ND |
|  |  |  |  |  | RhoA T19N | ND | ND | ND |
|  |  |  |  |  | Rac Q61L | ND | ND | ND |
| 5SP11 | X | 0 | X | X | RhoA Q63L | ND | ND | ND |
|  |  |  |  |  | RhoB Q63L | ND | ND | ND |
|  |  |  |  |  | RhoC Q63L | ND | ND | ND |
|  |  |  |  |  | RhoA T19N | ND | ND | ND |
|  |  |  |  |  | Rac Q61L | ND | ND | ND |
| 5SP58 | X | 0 | X | X | RhoA Q63L | ND | ND | ND |
|  |  |  |  |  | RhoB Q63L | ND | ND | ND |
|  |  |  |  |  | RhoC Q63L | ND | ND | ND |
|  |  |  |  |  | RhoA T19N | ND | ND | ND |
|  |  |  |  |  | Rac Q61L | ND | ND | ND |
| 5SNP47 | X | 0 | X | X | RhoA Q63L | ND | ND | ND |
|  |  |  |  |  | RhoB Q63L | ND | ND | ND |
|  |  |  |  |  | RhoC Q63L | ND | ND | ND |
|  |  |  |  |  | RhoA T19N | ND | ND | ND |
|  |  |  |  |  | Rac Q61L | ND | ND | ND |
| 5SNP48 | X | 0 | X | X | RhoA Q63L | 8.14+5 | 6.86−4 | 8.42 10 = 0.84 nM |
|  |  |  |  |  | RhoB Q63L | 4.62+5 | 0.0024 | 5.21−9 = 5.21 nM |
|  |  |  |  |  | RhoC Q63L | 1.72+6 | 9.01−4 | 5.24−10 = 0.524 nM |
|  |  |  |  |  | RhoA T19N | négatif | négatif | négatif |
|  |  |  |  |  | Rac Q61L | ND | ND | ND |
| 5SNP65 | X | 0 | X | X | RhoA Q63L | 8.70+5 | 5.22−4 | 6.00−10 = 0.600 nM |
|  |  |  |  |  | RhoB Q63L | 2.53+5 | 5.99−4 | 2.36−9 = 2.36 nM |
|  |  |  |  |  | RhoC Q63L | 1.71+6 | 0.001 | 6.08−10 = 0.608 nM |
|  |  |  |  |  | RhoA T19N | négatif | négatif | négatif |
|  |  |  |  |  | Rac Q61L | ND | ND | ND |
| B6 | ND | X | X | X | RhoA Q63L | 1.05 | 0.8 | 1.3125 nM |
|  |  |  |  |  | RhoB Q63L | 1.1 | 1.55 | 0.70969 nM |
|  |  |  |  |  | RhoC Q63L | 1.45 | 0.625 | 2.32 nM |

(ND = non determined)

Example 2: Functional Characterization of the H12 Antibody

The clone H12 was further analyzed by ELISA, using in this case the soluble form of the antibody, on several purified Rho proteins expressed as GST fusion in *E. coli*. We showed that the H12 hs2dAb efficiently bound to the constitutively active mutant RhoA$_{L63}$ as well as to wild type RhoA loaded with GTPγS. In contrast, no binding was observed to the inactive RhoA$_{N19}$ mutant or to GDP-loaded wild type RhoA (FIG. 1A). We then tested whether H12 was able to specifically pull-down GTP-loaded RhoA from mammalian cell extracts. A CBD tagged H12 construct expressed in *E. coli* was immobilized on chitin beads and incubated with a HeLa cell extract pre-treated with either GTPγS or GDP. The Rho binding domain of Rhotekin fused to GST (GST-RBD) was used as a control. This domain is known to bind to the active conformation of Rho GTPase and is the standard method to assay Rho activity up to now. The H12 hs2dAb was found to be highly selective of Rho loaded with GTPγS, giving no signal on the GDP loaded extract (FIG. 1B). We next tested whether H12 specifically detected RhoA active conformation in immunofluorescence. HeLa cells expressing the GFP-RhoA$_{L63}$ active mutant or the inactive GFP-RhoA, were fixed and stained with the H12 hs2dAb.

Overexpression of the inactive mutant GFP-RhoA$_{N19}$, which has no dominant negative effect on RhoA pathway nor on cell shape, did not lead to an increased signal over the background of untransfected cells. In contrast, a strong staining was selectively obtained on cells expressing the GFP-RhoA$_{L63}$ active mutant. Note that these cells display bundled actin stress fibers, a characteristic phenotype linked to enhanced RhoA activity (FIG. 1B). Altogether these results showed that the H12 hs2dAb is selective for Rho in its active conformation.

Furthermore our results suggest that the H12 antibody was able to perturb endogenous Rho activity when expressed in the cytosol. First, we co-expressed H12-GFP in HeLa cells together with either the RhoA$_{N19}$ inactive mutant or with the RHoA$_{L63}$ constitutively active one and carried out a co-immunoprecipitation experiment using an anti-GFP monoclonal antibody. Active RhoA was co-immunoprecipated with H12-GFP while inactive RhoA was not. This showed that H12 worked as an intrabody and kept its conformation sensitivity in the cytosol. Because Rho GTPases are involved in signaling pathways that promotes the actin cytoskeleton polymerization we looked at functional effects induced by H12 overexpression. In contrast to untransfected cells or cells transfected with various non-relevant GFP fused hs2dAb, we observed that cells expressing H12-GFP were totally devoid of actin stress fibers (FIG. 2). This alteration in actin filament organization was associated with marked changed in cell shape characteristic of loss of intracellular mechanical forces and tension (FIG. 2). As RhoA plays a major role in activating myosin II and actin cytoskeleton reorganization, our results suggested that H12 efficiently perturbed Rho-dependent signaling, mimicking the effects induced by the C3 exoenzyme Rho inhibitor.

Example 3: Functionalization Conformational Intrabodies to Target RhoB Activity

Direct Selection of Intrabodies by Visual Screen of Fluorescent Protein Knock Down In the goal of interfering with RhoB activity in cells using intrabodies, we established a strategy starting with a phage display selection then followed by in-cell screening aiming at the identification of a functional inhibitory intrabody. In the past decade we established sophisticated phage display selection scheme in order to isolate binders discriminating the GTP conformation of Rho proteins. To preserve the native conformation of RhoB during the selection, bait antigens were expressed in mammalian cells and freshly extracted and used in the nanomolar range during the incubation with the NaLi-H1 library phages. A competitive panning selection was carried out using a constitutively active mutant RhoBL63 after a preclearing step in the presence of an excess of GDP loaded wild type RhoB to enrich in binders more selective towards RhoB than its closest homologs. After two round of enrichment, we added a 5 molar excess of RhoAL63 and RhoCL63 to further compete with the bait. After controlling positive enrichment of binding phages to a bacterially expressed and purified GTS-RhoBL63 in phage ELISA, we wanted to develop a direct screening for RhoB intrabodies. We learned from our previous experiences in recombinant antibody technologies that such monoclonal binding domains efficacy can be very assay-dependent, namely that positive one in ELISA screen often failed to work in immunofluorescence or vice versa.

We also isolated intrabodies using a selection scheme base on co-localization of a fluorescent fusion of the nanobody with the target. Then when we functionalized a set of these tracking intrabodies, replacing the GFP by a proteasome targeting domain to degrade the antigen, there was surprisingly no obvious correlation between the best trackers and the best degraders. Therefore we reasoned that the best way to identify an intrabody that work in a specific assay would be to screen directly in the final format.

Here we chose to inhibit RhoB by inducing its proteasome mediated degradation. Several functionalization of intrabodies mend to induce degradation of the target. One of them consists in fusing the Fbox domain of an Fbox protein. Fbox protein contains two modular domains, one for target recognition and the Fbox domain that interact with Skip1, a component of the SCF E3 ubiquitin ligase complex, which induce polyubiquitinylation of the Fbox protein target followed by subsequent proteasomal degradation. Replacement of the target binding domain with an intrabody can specify the target, therefore inducing degradation of the antigen. One advantage of that knockdown strategy is that the Fbox-intrabody (F-Ib) act in a catalytic manner and is not co-degraded. Another one resides in the fact that if degradation is observed, this report indirectly the intracellular interaction between the antigen and the nanobody. The main drawback can be that the targeted antigen does not display ubiquitinylation site, but it is not the case for small GTPases or any protein that could be degraded naturally by the proteasome. We have previously tested this strategy for several anti-GFP hs2dAb intrabodies and constructed a plasmid which allows the expression of an amino terminal Fbox domain from *Drosophila* slmb gene fused to hs2dAb and a carboxy terminal myc tag upstream of a mitochondrial fluorescent reporter gene expressed as a second cistron translated from an IRES. We choose to set up a visual screen of target degradation by fusing RhoB to a fluorescent protein. To mimic active RhoB, we choose to express a constitutively active mutant RhoBL63, which is strongly impaired in catalyzing GTP nucleotide hydrolysis, thus remains in the GTP loaded active state. To avoid binding crosstalk with endogenous RhoB, we used a RHOB−/− lung epithelial cell line H2882. As RhoBL63 expression toxicity did not allow us to produce a stable cell line, we constructed a chimera which consist in a sequence coding an amino terminal histone H2B, followed by the mCherry fluorescent protein and a carboxy terminal RhoBL63 deleted for the 5 terminal amino acid that correspond to the palmitoylation and prenylation signals. This fusion protein loss the membrane anchorage capacity and was artificially incorporated to the chromatin nucleosomes, giving a fluorescent signal in the nucleus while displaying active RhoBL63 mutant at a localization which appeared to be nontoxic to generate a stable cell line, referred as HmB. To control the binding specificity to RhoBL63, a cell line expressing only H2B-mCherry was generated as well, referred as Hm. We hypothesized that if a Fbox-hs2dAb is a stable F-Ib and if interaction occurs specifically with RhoBL63, a decrease of nuclear mCherry fluorescence would be observed in the HmB cell line but not in the Hm one. Therefore a fluorescence decay correlated to RhoBL63 degradation could be the basis of a visual screening for F-Ib RhoB inhibitors. Chromatin quantity and density is cell-dependent, fluctuating according to the cell cycle, giving a slight heterogeneity in the cell nuclear fluorescence could. Another source of cell-dependent heterogeneity in a screen based on transient plasmid transfection comes from the variable plasmid copy number, the transfection efficiency and the relative expression level of F-Ib. To better assess these parameter, we used our F-Ib bi-cistronic expression vector with a monomeric GFP targeted to the mitochondrial matrix as a reporter gene and set up the assay using two negative hs2dAb in this screening, referred as F-NR that is non relevant to RhoB phage display and the F-20, previously selected towards RhoB but that is not a degrading intrabody. In summary, the visual screen resides in the observation of mCherry nuclear fluorescence decay in cells showing GFP fluorescent mitochondria.

Figure 3A:
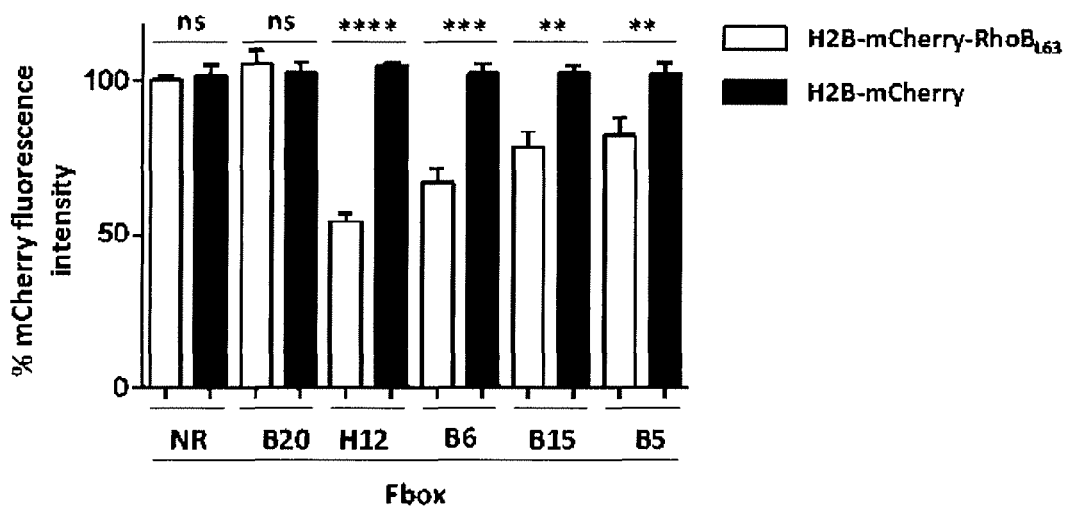

After 4 rounds of panning, hs2dAb sequence were digested in pool and directly inserted in the F-Ib bicistronic vector. Although such polyclonal subcloning could lead to a certain extend to diversity loss compared to the phagemid sublibrary, we reasoned that in conventional phage display strategies, only a set of randomly picked colonies are screened and that the effective enrichment of specific binders during phage selection have less probability to be not transferred during subcloning. After a single cloning step, we screened several hundred of F-hs2dAb, by transient transfection of individual plasmid clones in both cell lines (HmB and Hm), and observed the mCherry fluorescence intensity on an inverted microscope. After sequencing positive hits, we identified four unique clones that induced a strong decay of mCherry fluorescence in HmB cell transfected cells only in comparison with to the two negative internal controls F-NR and F-20. One of the selected clones was the H12 hs2dAb, which is the pan active Rho that was previously identified from that NaLi-H1 library. The fluorescent decay quantification on some selected field suggested that these F-Ib were inducing degradation of H2B-mCherry-RhoBL63 depending on the presence of RhoBL63. Then, these results were further quantified by flow cytometry, confirming that F-H12, F-B6, F-B15 and F-B5 degrade selectively H2BmCherry-RhoBL63 and showing that F-H12 and F-B6 are the most efficient F-Ib (FIG. 3A).

Characterization of Selected F-Ib

Figure 3B:
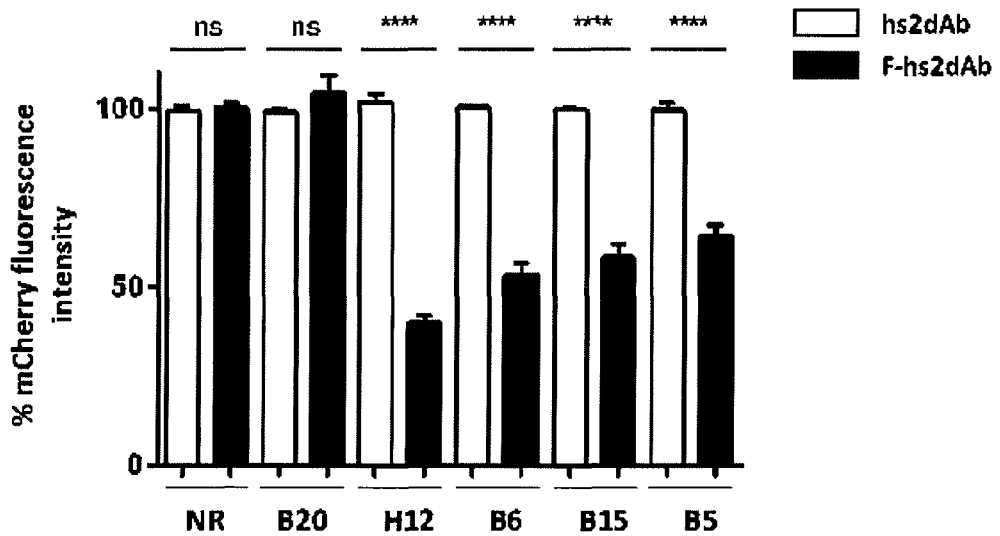
Figure 3C:
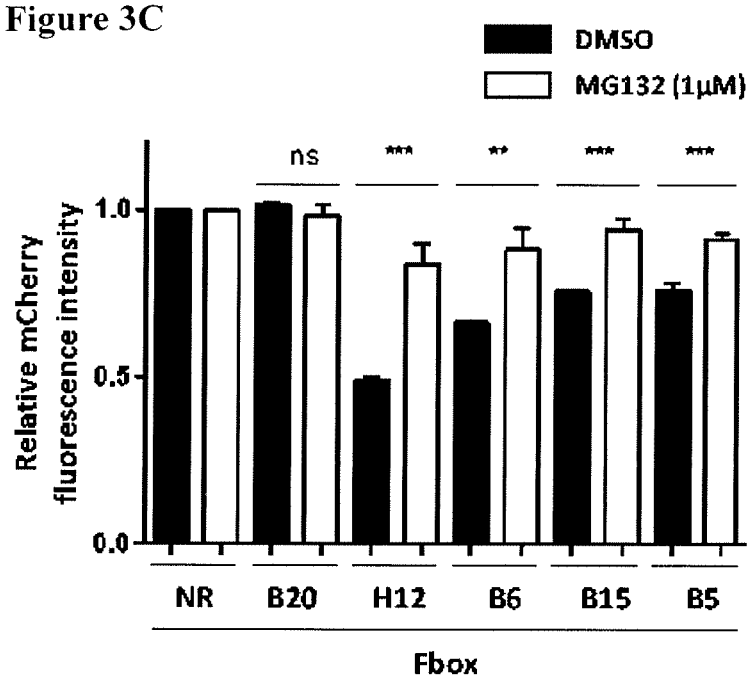

The fusion of a Fbox domain to a peptide or an intrabody have been reported to mediate target degradation by the proteasome in various cellular context. To confirm whether the presence of the Fbox domain was responsible to the degradation, we expressed hs2dAb alone in Hm and HmB cell lines and observed no decrease in mCherry fluorescence (FIG. 3B). Next, using the MG132 proteasome inhibitor, we controlled that the observed degradation was proteasome dependent. In comparison to DMSO treatment that barely reduce the 4 F-Ib induced fluorescent decay quantified by flow cytometry, the treatment at 1 µM of MG132 during 36 h restored the mCherry fluorescence almost to the control level (FIG. 3C). Finally we analyzed whether the fluorescence decay was a direct effect of the F-Ib expression by quantifying the fluorescence after decreasing the concentration of plasmid in the transfection from 2 µg to 0. A dose-response direct effect was observed for the effective F-H12 and F-B6, as the lower was the plasmid concentration the higher was the fluorescence signal (data not shown). Together these results demonstrated that the F-Ib selected by the direct visual screening were specifically targeting and degrading in a proteasome dependent manner the RhoBL63 delta CAAX protein concentrated on the chromatin.

Specificity and Conformational Selectivity of the Selected F-Ib

Figure 3D:
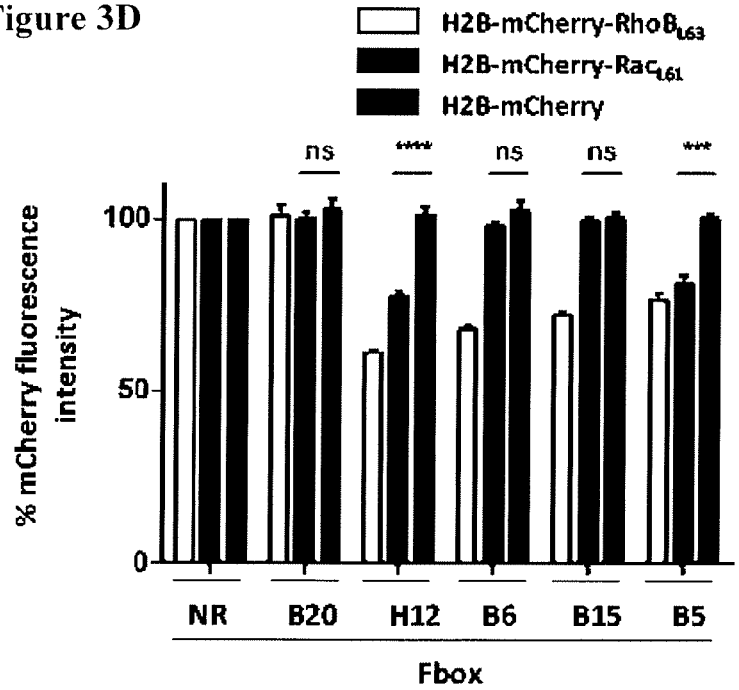
Figure 3E:
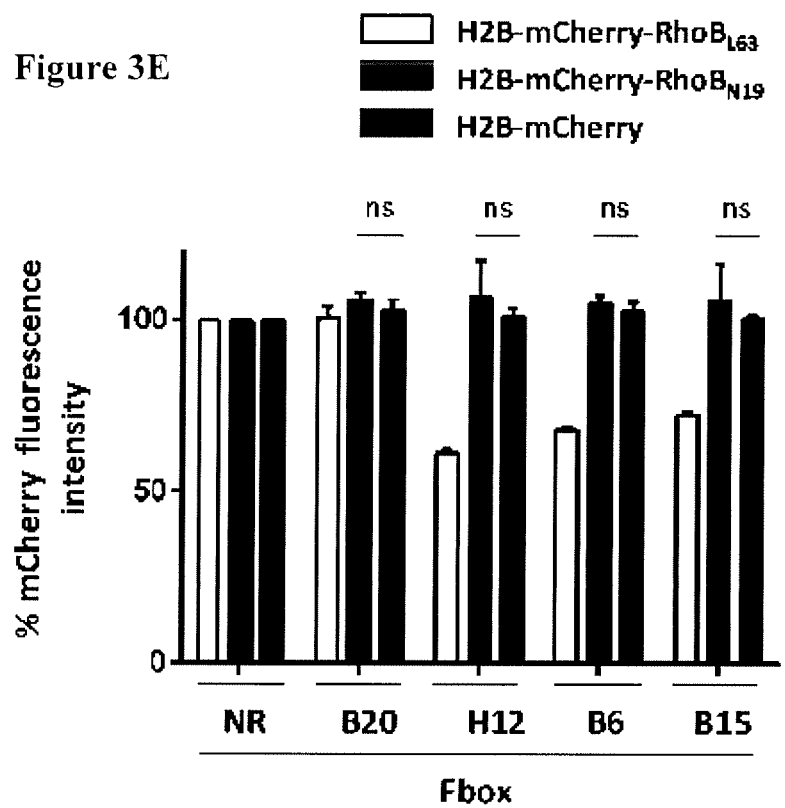

The H12 hs2dAb is a conformational sensor and a blocking intrabody of the GTP loaded Rho proteins without distinction between RhoA, RhoB, RhoC homologs and even recognizing Rac1 and CDCl42 closely related GTPases. The fact that it was enriched and selected again in this study was not surprising as in previous panning its enrichment was very high in the early round of selection as its representation was above 50% of the clones at the third round of panning on RhoAL63. Despite here we introduced competition with active RhoA and RhoC, H12 was not totally eliminated from the selection, suggesting that others newly selected hs2dAb could also be pan Rho as well. Nevertheless H12 enrichment was much lower, suggesting that the new subtractive selection was at least partially efficient. To determine the selectivity of the selected F-hs2dAb, we produced different stable cell lines on the same basis than H2B-mCherry-RhoBL63. Transfection of H2B-mCherry-RhoAL63 and H2B-mCherry-RhoCL63 failed to produce stable cell line and the heterogeneity of transient expression did not lead to conclusive quantification of fluorescence decay (data not shown). However the generation of a similar cell line was possible with H2B-mCherry-Rac1L61, Rac1 being the closest homolog of the Rho subfamily mainly in the switch domains. As expected, F-H12 induced a fluorescence decay in the later cell line. Among the other selected F-Ib, F-B5 was also affecting the fluorescence level of the H2B-mCherry-Rac1L63 but F-B6 and F-B15 failed to degrade the active form of Rac1 (FIG. 3D). At this point we pursued the study without the hs2dAb 5 or its F-5 functionalization but we kept the hs2dAb H12 as a pan active Rho control. Then we addressed the conformational selectivity of the remaining F-Ib by comparing their effect on a RhoBN19 mutant which is supposed to be mainly inactive as the same mutation lead to a GTPase defective in the nucleotide binding for other Ras homologs. We generated a H2B-mCherry-RhoBN19 stable cell line in order to determine the conformational selectivity hs2dAb expressed as F-Ib in our fluorescence decay assay. After FACS analysis, all effective F-Ib were degrading only the active mutant of RhoB and not the inactive form (FIG. 3E). These results indicate that F-B6 and F-B15 are conformational hs2dAb that preferentially recognize RhoB in its active conformation.

Endogenous RhoB Activity Knockdown

Figure 4A:
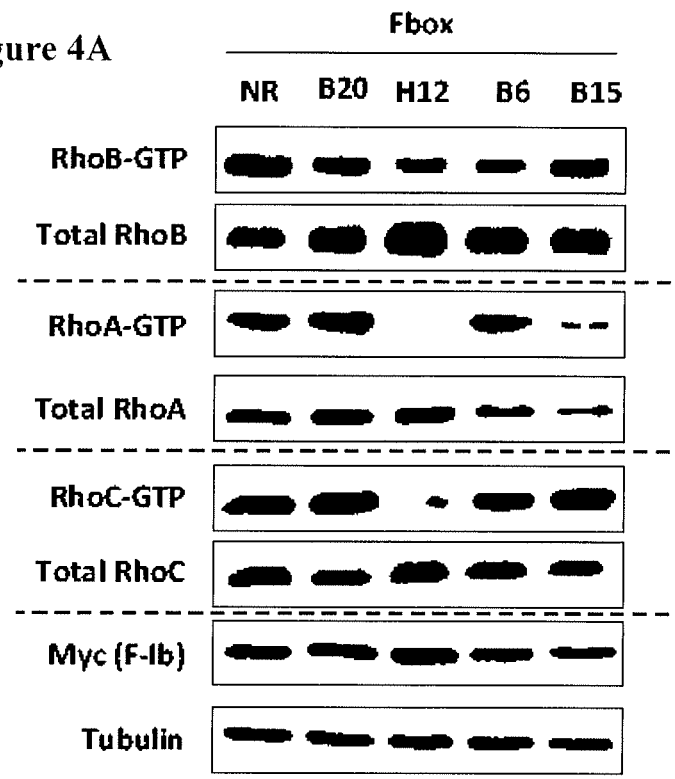
Figure 4B:
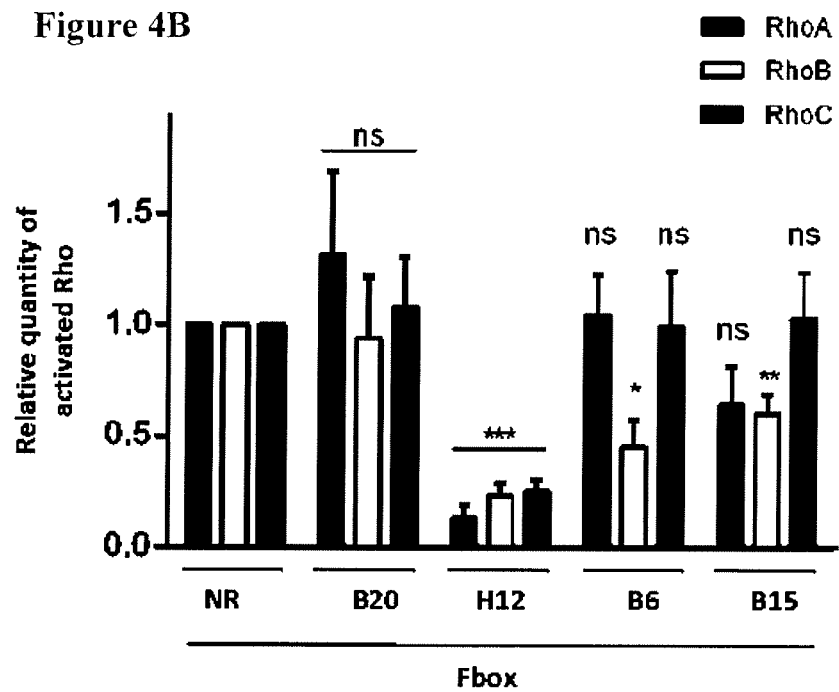

We then investigated whether these intrabodies were able to degrade the endogenous active form of RhoB. To this end we used HeLa S3 cells, a common cell line that express significant amount of RhoB protein with a detectable basal level of active RhoB. The standard method to assay the Rho GTPase activity is based on a pull down using the GST-RBD. RBD is the Rho Binding Domain from Rhotekin, a common effector of the three Rho which interacts only with the GTP bound Rho. After 48 h of transient transfection of F-Ib, pull down of RhoB basal active fraction was lower in cells transfected by F-B6, F-B15 or F-H12 than with the controls F-B20 and F-NR. Detection of RhoA and RhoC allowed to assess whether their basal activities were also affected. As expected F-H12 induced a strong decrease in the level of all 3 Rho active fractions. However, the level of the 3 active Rho was not decreased equally for the F-B15 and F-B6 expression, suggesting that they do not have the same selectivity than F-H12. In contrast to the F-B15 hs2dAb that induced degradation of both active RhoB and RhoA, F-B6 did not induced apparent modulation of RhoA or RhoC pulled down fractions (FIG. 4A). Quantifications indicated that F-B6 degrades solely RhoB activity in this cellular context and assay conditions (FIG. 4B). This result is the first example of a molecule which would discriminate RhoB from RhoA in their GTP loaded state and that would enable their cellular proteolysis.

Figure 4C:
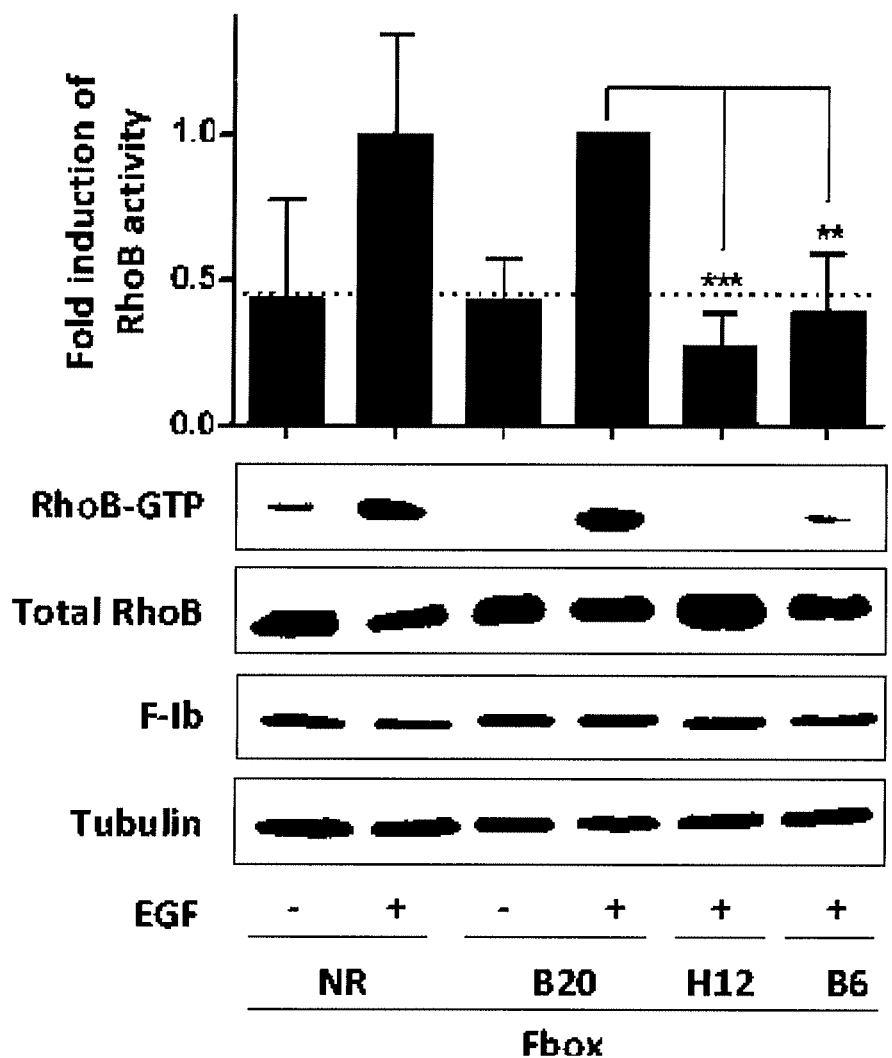
Figure 4D:
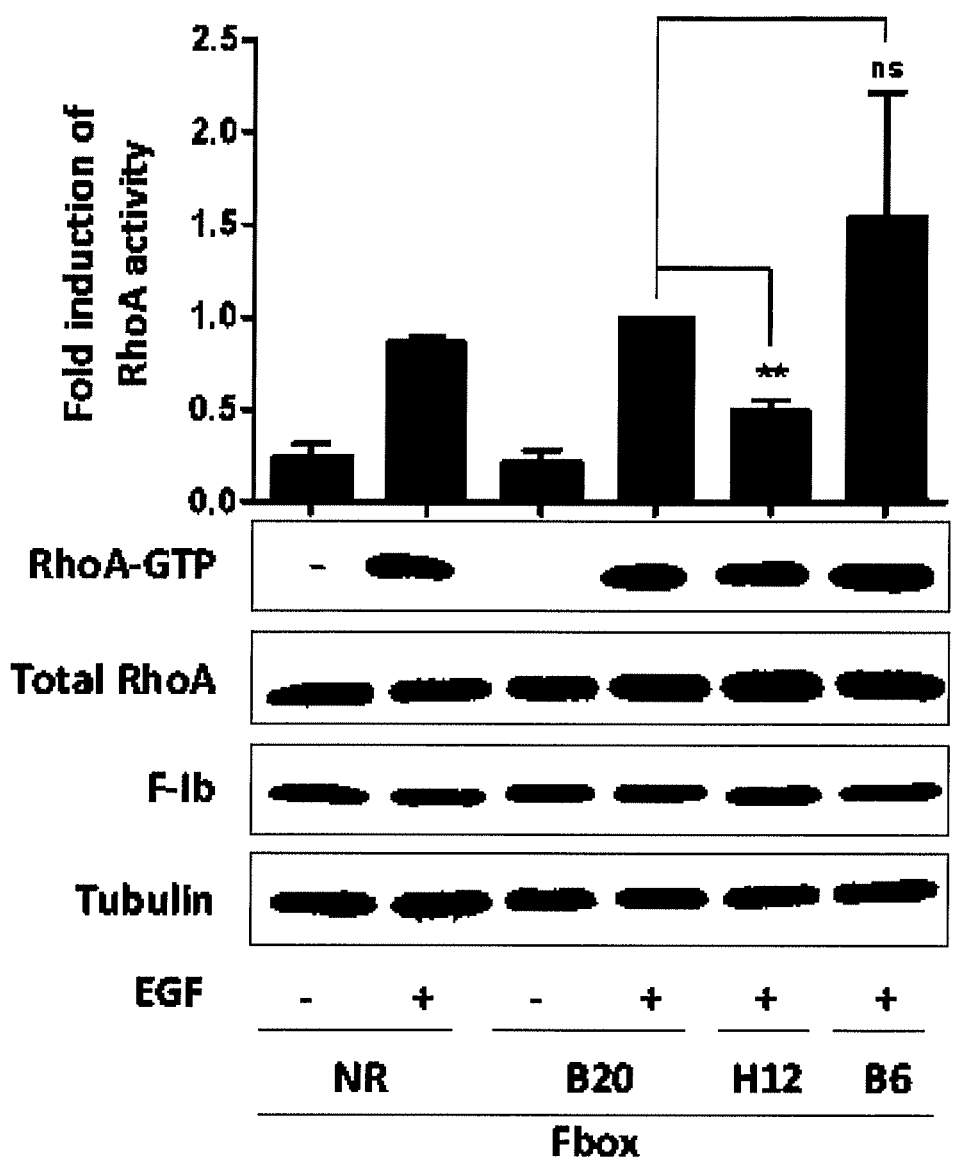
Figure 4E:
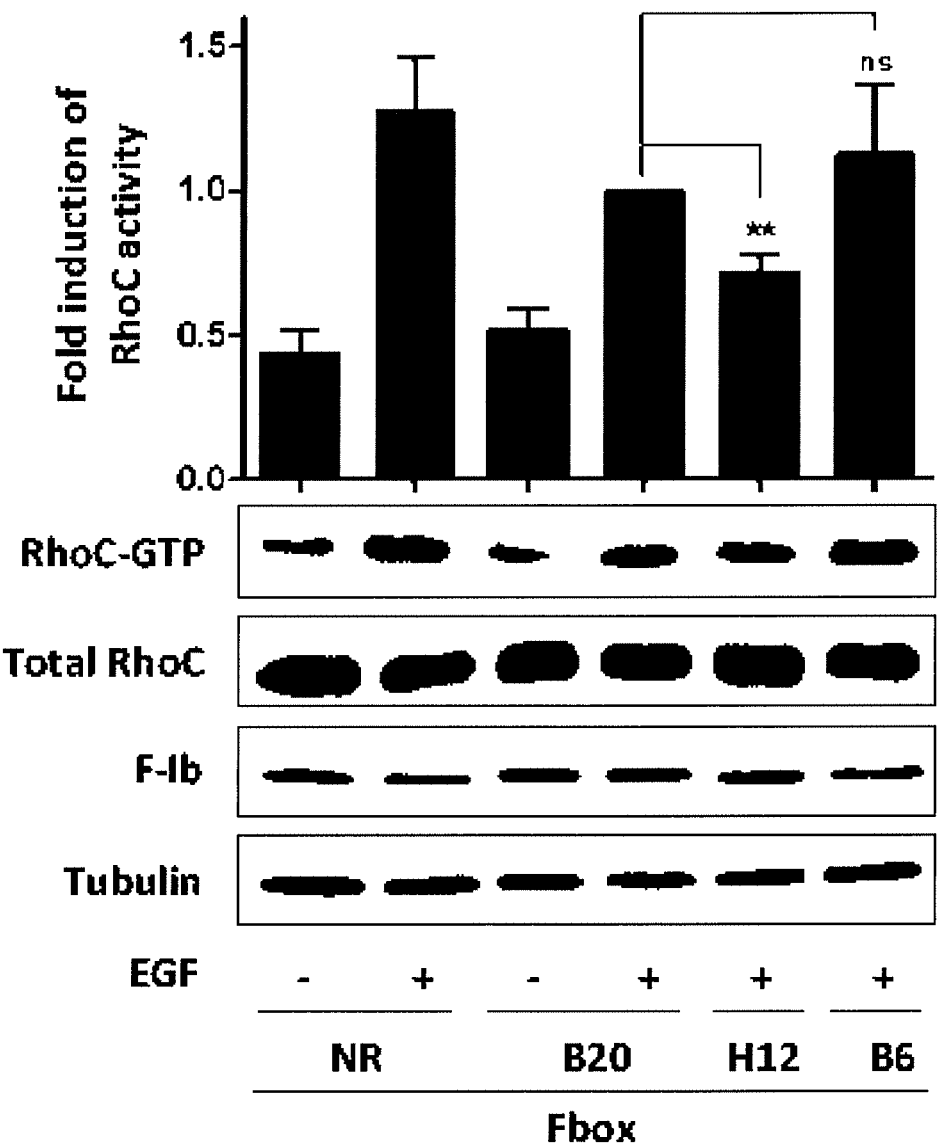

To investigate whether the protein knockdown observed 48 h post transfection with the F-6 was direct and specific, we targeted the fast process of cellular activation of Rho proteins. Actually RhoB and RhoA, and to a lesser extend RhoC, have been reported to be activated in few minutes after an EGF treatment. After 24 h of serum starvation, activation kinetics of each Rho by EGF was assessed in HeLaS3 cells. Activation was observed as soon as 5 minutes after stimulation for all 3 Rho and reached a maximum at 15 minutes, which was chosen as activation time for further experiments (FIGS. 4C & 4D). We characterized the effect of F-H12 and F-B6 on Rho activation and confirmed the selective observed degradation of RhoA/B activity. While F-NR or F-B20 controls did not prevent EGF mediated Rho activation, F-B6 degrades only RhoB activity induced by EGF whereas FH12 inhibit all Rho activities indeed (FIGS. 4C & 4D).

In conclusion, the hs2dAb B6 seems to be a RhoB-GTP very selective intrabody, which is able to block RhoB basal activity as well as its stimulated activation while functionalized as F-Ib, without down regulating major fraction of cellular RhoB.

REFERENCES

Throughout this application, various references describe the state of the art to which this invention pertains. The disclosures of these references are hereby incorporated by reference into the present disclosure.

We claim:

1. A nucleic acid molecule which encodes a single domain antibody, wherein the amino acid sequences of CDR1-IMGT, CDR2-IMGT and CDR3-IMGT of the single domain antibody are set forth as SEQ ID NOS: 5-7.

2. A vector which includes the nucleic acid molecule of claim 1.

3. A host cell transformed with the nucleic acid molecule of claim 1.

* * * * *

SEQUENCE LISTING

```
<160> NUMBER OF SEQ ID NOS: 96

<210> SEQ ID NO 1
<211> LENGTH: 25
<212> TYPE: PRT
<213> ORGANISM: Artificial
<220> FEATURE:
<223> OTHER INFORMATION: Synthetic FR1

<400> SEQUENCE: 1

Val Gln Leu Gln Ala Ser Gly Gly Gly Phe Val Gln Pro Gly Gly Ser
1               5                   10                  15

Leu Arg Leu Ser Cys Ala Ala Ser Gly
            20                  25

<210> SEQ ID NO 2
<211> LENGTH: 20
<212> TYPE: PRT
<213> ORGANISM: Artificial
<220> FEATURE:
<223> OTHER INFORMATION: Synthetic FR2

<400> SEQUENCE: 2

Met Gly Trp Phe Arg Gln Ala Pro Gly Lys Glu Arg Glu Phe Val Ser
1               5                   10                  15

Ala Ile Ser Ser
            20

<210> SEQ ID NO 3
<211> LENGTH: 39
<212> TYPE: PRT
<213> ORGANISM: Artificial
<220> FEATURE:
<223> OTHER INFORMATION: Synthetic FR3

<400> SEQUENCE: 3

Tyr Tyr Ala Asp Ser Val Lys Gly Arg Phe Thr Ile Ser Arg Asp Asn
1               5                   10                  15

Ser Lys Asn Thr Val Tyr Leu Gln Met Asn Ser Leu Arg Ala Glu Asp
            20                  25                  30

Thr Ala Thr Tyr Tyr Cys Ala
        35

<210> SEQ ID NO 4
<211> LENGTH: 12
<212> TYPE: PRT
<213> ORGANISM: Artificial
<220> FEATURE:
<223> OTHER INFORMATION: Synthetic FR4
```

```
<400> SEQUENCE: 4

Tyr Trp Gly Gln Gly Thr Gln Val Thr Val Ser Ser
1               5                   10

<210> SEQ ID NO 5
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 5

Asp Gly Ser Arg Ile Tyr Ala
1               5

<210> SEQ ID NO 6
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 6

Trp Glu Gln Asp Trp Glu His
1               5

<210> SEQ ID NO 7
<211> LENGTH: 12
<212> TYPE: PRT
<213> ORGANISM: Artificial
<220> FEATURE:
<223> OTHER INFORMATION: Synthetic CDR3-IMGT

<400> SEQUENCE: 7

Ala Phe Met Thr Pro His Arg Asn Leu Thr Ser Met
1               5                   10

<210> SEQ ID NO 8
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 8

Arg Tyr Ser Ala Trp Asp Gly
1               5

<210> SEQ ID NO 9
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 9

Ser Gln His Asp Leu Glu Glu
1               5

<210> SEQ ID NO 10
<211> LENGTH: 9
<212> TYPE: PRT
<213> ORGANISM: Artificial
<220> FEATURE:
<223> OTHER INFORMATION: Synthetic CDR3-IMGT

<400> SEQUENCE: 10
```

```
Ala Thr Ile Arg Thr Gly Trp Ala Asp
1               5

<210> SEQ ID NO 11
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 11

Asp Thr Ser Asp Gly Tyr Ile
1               5

<210> SEQ ID NO 12
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 12

Glu Tyr Asn Ser Gln Ser Glu
1               5

<210> SEQ ID NO 13
<211> LENGTH: 15
<212> TYPE: PRT
<213> ORGANISM: Artificial
<220> FEATURE:
<223> OTHER INFORMATION: Synthetic CDR3-IMGT

<400> SEQUENCE: 13

Gln Ser Phe Asn Glu Val Trp Lys Met Pro Asn Lys Phe Pro His
1               5                   10                  15

<210> SEQ ID NO 14
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 14

Thr Ser Trp Lys Asp Tyr Thr
1               5

<210> SEQ ID NO 15
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 15

Glu Gly Pro Gly Ala Gln Tyr
1               5

<210> SEQ ID NO 16
<211> LENGTH: 9
<212> TYPE: PRT
<213> ORGANISM: Artificial
<220> FEATURE:
<223> OTHER INFORMATION: Synthetic CDR3-IMGT

<400> SEQUENCE: 16
```

```
Tyr Ser Ser Trp Gln Pro Tyr Val Ser
1               5

<210> SEQ ID NO 17
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 17

Phe Thr Ser Thr Ser Thr Val
1               5

<210> SEQ ID NO 18
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 18

Ser Ala His Thr Met Asp Thr
1               5

<210> SEQ ID NO 19
<211> LENGTH: 18
<212> TYPE: PRT
<213> ORGANISM: Artificial
<220> FEATURE:
<223> OTHER INFORMATION: Synthetic CDR3-IMGT

<400> SEQUENCE: 19

Tyr Cys Ala Pro Ala Pro Met Leu Gly Gln Met Ile Thr Gln Pro Ala
1               5                   10                  15

Leu Pro

<210> SEQ ID NO 20
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 20

Arg Phe Trp Arg Arg Tyr Thr
1               5

<210> SEQ ID NO 21
<211> LENGTH: 6
<212> TYPE: PRT
<213> ORGANISM: Artificial
<220> FEATURE:
<223> OTHER INFORMATION: Synthetic CDR2-IMGT

<400> SEQUENCE: 21

Gly Thr Ser Asp Trp Thr
1               5

<210> SEQ ID NO 22
<211> LENGTH: 9
<212> TYPE: PRT
<213> ORGANISM: Artificial
<220> FEATURE:
<223> OTHER INFORMATION: Synthetic CDR3-IMGT

<400> SEQUENCE: 22
```

Pro Pro His Phe Ser Gly Ala Ala Ile
1               5

<210> SEQ ID NO 23
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 23

Ala Gly Trp Arg Ala Glu Ala
1               5

<210> SEQ ID NO 24
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 24

Ser Asp Gly Asp His Thr Ile
1               5

<210> SEQ ID NO 25
<211> LENGTH: 14
<212> TYPE: PRT
<213> ORGANISM: Artificial
<220> FEATURE:
<223> OTHER INFORMATION: Synthetic CDR3-IMGT

<400> SEQUENCE: 25

Ile Met Gln Thr Gln Met Arg Arg Thr Ser Asp Tyr Arg Phe
1               5                   10

<210> SEQ ID NO 26
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 26

Asp Thr Phe Ser Asp Asp Val
1               5

<210> SEQ ID NO 27
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 27

Asp Trp Pro Thr Thr Gln Ser
1               5

<210> SEQ ID NO 28
<211> LENGTH: 19
<212> TYPE: PRT
<213> ORGANISM: Artificial
<220> FEATURE:
<223> OTHER INFORMATION: Synthetic CDR3-IMGT

<400> SEQUENCE: 28

Tyr Cys Ala Gln Ala Asn Gly Asp His Ser Tyr Pro Leu Trp Lys Tyr
1               5                   10                  15

Gly Asn Met

<210> SEQ ID NO 29
<211> LENGTH: 7
<212> TYPE: PRT
<213> ORGANISM: Artificial
<220> FEATURE:
<223> OTHER INFORMATION: Synthetic CD1-IMGT

<400> SEQUENCE: 29

Arg Thr Ser Arg Phe Tyr Ser
1               5

<210> SEQ ID NO 30
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 30

Phe Asn Ser Asp Tyr Phe Leu
1               5

<210> SEQ ID NO 31
<211> LENGTH: 12
<212> TYPE: PRT
<213> ORGANISM: Artificial
<220> FEATURE:
<223> OTHER INFORMATION: Synthetic CDR3-IMGT

<400> SEQUENCE: 31

Ala Trp Trp Tyr Arg Tyr Thr Glu Gly Met Thr Met
1               5                   10

<210> SEQ ID NO 32
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 32

Thr Ser Trp Phe Thr Glu Val
1               5

<210> SEQ ID NO 33
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 33

Gly Leu His Asp Val Gly Thr
1               5

<210> SEQ ID NO 34
<211> LENGTH: 15
<212> TYPE: PRT
<213> ORGANISM: Artificial
<220> FEATURE:
<223> OTHER INFORMATION: Synthetic CDR3-IMGT

<400> SEQUENCE: 34

Ala Leu Asp Lys Trp Tyr Thr Lys Ala Met Asp Ala Arg Lys Asp
1               5                   10                  15

<210> SEQ ID NO 35
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 35

Ala Thr Tyr Glu Gly Glu Ala
1               5

<210> SEQ ID NO 36
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 36

Ser Tyr Pro Ser Val Ile Ser
1               5

<210> SEQ ID NO 37
<211> LENGTH: 12
<212> TYPE: PRT
<213> ORGANISM: Artificial
<220> FEATURE:
<223> OTHER INFORMATION: Synthetic CDR2-IMGT

<400> SEQUENCE: 37

Tyr Trp Val Asn His Glu Gly Thr Ile Arg Glu Ile
1               5                   10

<210> SEQ ID NO 38
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 38

Tyr Gly Ser Thr Ile Glu Thr
1               5

<210> SEQ ID NO 39
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 39

Arg Ala Pro Gly Pro Ser Gln
1               5

<210> SEQ ID NO 40
<211> LENGTH: 15
<212> TYPE: PRT
<213> ORGANISM: Artificial
<220> FEATURE:
<223> OTHER INFORMATION: Synthetic CDR3-IMGT

<400> SEQUENCE: 40

```
Pro Ile Asn Asn Arg Thr Met Gln Asp Ser Met Phe Leu Trp Asn
1               5                   10                  15

<210> SEQ ID NO 41
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 41

Thr Thr Ser Phe Trp Tyr Thr
1               5

<210> SEQ ID NO 42
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 42

Trp Arg Phe Asn Thr Thr Thr
1               5

<210> SEQ ID NO 43
<211> LENGTH: 15
<212> TYPE: PRT
<213> ORGANISM: Artificial
<220> FEATURE:
<223> OTHER INFORMATION: Synthetic CDR3-IMGT

<400> SEQUENCE: 43

Ile Pro Arg Tyr Ser Leu Asp Ala Val Pro His Arg Ala Ser Thr
1               5                   10                  15

<210> SEQ ID NO 44
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 44

Ser Tyr Ser Arg Gly Glu Thr
1               5

<210> SEQ ID NO 45
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 45

Asp Thr His Asn Tyr Glu Thr
1               5

<210> SEQ ID NO 46
<211> LENGTH: 15
<212> TYPE: PRT
<213> ORGANISM: Artificial
<220> FEATURE:
<223> OTHER INFORMATION: Synthetic CDR3-IMGT

<400> SEQUENCE: 46

Ala Ser Pro Gln Phe His Lys Ile Met Lys Gly Ser Gln Val Gly
```

<210> SEQ ID NO 47
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 47

Ala Thr Ser Gly Gly Thr Val
1               5

<210> SEQ ID NO 48
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 48

Arg Ser Gln Thr Lys Ala Thr
1               5

<210> SEQ ID NO 49
<211> LENGTH: 12
<212> TYPE: PRT
<213> ORGANISM: Artificial
<220> FEATURE:
<223> OTHER INFORMATION: Synthetic CDR"-IMGT

<400> SEQUENCE: 49

Pro Met Glu His Glu Ala Leu Lys Gln His Pro Leu
1               5                   10

<210> SEQ ID NO 50
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 50

Asp Gly Ser Asp Gly Asp Val
1               5

<210> SEQ ID NO 51
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 51

Arg Tyr Pro Gly Arg Ser Pro
1               5

<210> SEQ ID NO 52
<211> LENGTH: 15
<212> TYPE: PRT
<213> ORGANISM: Artificial
<220> FEATURE:
<223> OTHER INFORMATION: Synthetic CDR3-IMGT

<400> SEQUENCE: 52

Ala Arg Trp Ile Ser Arg Lys Trp Tyr Thr Thr Pro Phe Gln Gly
1               5                   10                  15

```
<210> SEQ ID NO 53
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 53

Ser Thr Tyr Glu Thr Tyr Ala
1               5

<210> SEQ ID NO 54
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 54

Ala Ser Pro Thr Ile Glu Gly
1               5

<210> SEQ ID NO 55
<211> LENGTH: 9
<212> TYPE: PRT
<213> ORGANISM: Artificial
<220> FEATURE:
<223> OTHER INFORMATION: Synthetic CDR3-IMGT

<400> SEQUENCE: 55

Thr Trp Ser Lys Met Gly Ile Ser Ile
1               5

<210> SEQ ID NO 56
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 56

Asp Thr Trp Asp Gln Tyr Val
1               5

<210> SEQ ID NO 57
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 57

Arg Ser Gly Thr His Gly Ile
1               5

<210> SEQ ID NO 58
<211> LENGTH: 12
<212> TYPE: PRT
<213> ORGANISM: Artificial
<220> FEATURE:
<223> OTHER INFORMATION: Synthetic CDR3-IMGT

<400> SEQUENCE: 58

Pro Leu Thr His Gln Trp Met Gly Arg Thr Phe Pro
1               5                   10
```

```
<210> SEQ ID NO 59
<211> LENGTH: 7
<212> TYPE: PRT
<213> ORGANISM: Artificial
<220> FEATURE:
<223> OTHER INFORMATION: Synthetic CDR1-IMGT

<400> SEQUENCE: 59

Arg Thr Ser Gly Trp Tyr Ala
1               5

<210> SEQ ID NO 60
<211> LENGTH: 7
<212> TYPE: PRT
<213> ORGANISM: Artificial
<220> FEATURE:
<223> OTHER INFORMATION: Synthetic CDR2-IMGT

<400> SEQUENCE: 60

Ser Arg Ala Ser Ser Gln Glu
1               5

<210> SEQ ID NO 61
<211> LENGTH: 9
<212> TYPE: PRT
<213> ORGANISM: Artificial
<220> FEATURE:
<223> OTHER INFORMATION: Synthetic CDR3-IMGT

<400> SEQUENCE: 61

Val Trp Met Lys Met Gly Ile Glu Ile
1               5

<210> SEQ ID NO 62
<211> LENGTH: 121
<212> TYPE: PRT
<213> ORGANISM: Artificial
<220> FEATURE:
<223> OTHER INFORMATION: Synthetic H12

<400> SEQUENCE: 62

Val Gln Leu Gln Ala Ser Gly Gly Gly Phe Val Gln Pro Gly Gly Ser
1               5                   10                  15

Leu Arg Leu Ser Cys Ala Ala Ser Gly Asp Gly Ser Arg Ile Tyr Ala
            20                  25                  30

Met Gly Trp Phe Arg Gln Ala Pro Gly Lys Glu Arg Glu Phe Val Ser
        35                  40                  45

Ala Ile Ser Trp Glu Gln Asp Trp Glu His Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Phe Met Thr Pro His Arg Asn Leu Thr Ser Met Tyr Trp Gly
            100                 105                 110

Gln Gly Thr Gln Val Thr Val Ser Ser
        115                 120

<210> SEQ ID NO 63
<211> LENGTH: 117
<212> TYPE: PRT
<213> ORGANISM: Artificial
<220> FEATURE:
```

<223> OTHER INFORMATION: Synthetic 4P75

<400> SEQUENCE: 63

Val Gln Leu Gln Ala Ser Gly Gly Gly Phe Val Gln Pro Gly Gly Ser
1               5                   10                  15

Leu Arg Leu Ser Cys Ala Ala Ser Gly Arg Tyr Ser Ala Trp Asp Gly
            20                  25                  30

Met Gly Trp Phe Arg Gln Ala Pro Gly Lys Glu Arg Glu Phe Val Ser
        35                  40                  45

Ala Ile Ser Ser Gln His Asp Leu Glu Glu Tyr Tyr Ala Asp Ser Val
    50                  55                  60

Lys Gly Arg Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Tyr Cys Ala
                85                  90                  95

Ala Thr Ile Arg Thr Gly Trp Ala Asp Tyr Trp Gly Gln Gly Thr Gln
            100                 105                 110

Val Thr Val Ser Ser
            115

<210> SEQ ID NO 64
<211> LENGTH: 124
<212> TYPE: PRT
<213> ORGANISM: Artificial
<220> FEATURE:
<223> OTHER INFORMATION: Synthetic 4SP1

<400> SEQUENCE: 64

Val Gln Leu Gln Ala Ser Gly Gly Gly Phe Val Gln Pro Gly Gly Ser
1               5                   10                  15

Leu Arg Leu Ser Cys Ala Ala Ser Gly Asp Thr Ser Asp Gly Tyr Ile
            20                  25                  30

Met Gly Trp Phe Arg Gln Ala Pro Gly Lys Glu Arg Glu Phe Val Ser
        35                  40                  45

Ala Ile Ser Glu Tyr Asn Ser Gln Ser Glu Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Gln Ser Phe Asn Glu Val Trp Lys Met Pro Asn Lys Phe Pro His
            100                 105                 110

Tyr Trp Gly Gln Gly Thr Gln Val Thr Val Ser Ser
        115                 120

<210> SEQ ID NO 65
<211> LENGTH: 117
<212> TYPE: PRT
<213> ORGANISM: Artificial
<220> FEATURE:
<223> OTHER INFORMATION: Synthetic 4SNP63

<400> SEQUENCE: 65

Val Gln Leu Gln Ala Ser Gly Gly Gly Phe Val Gln Pro Gly Gly Ser
1               5                   10                  15

Leu Arg Leu Ser Cys Ala Ala Ser Gly Thr Ser Trp Lys Asp Tyr Thr
            20                  25                  30

Met Gly Trp Phe Arg Gln Ala Pro Gly Lys Glu Arg Glu Phe Val Ser

```
                35                  40                  45
Ala Ile Ser Glu Gly Pro Gly Ala Gln Tyr Tyr Tyr Ala Asp Ser Val
        50                  55                  60

Lys Gly Arg Phe Thr Ile Ser Arg Asp Asn Ser Lys Asn Val Tyr Leu
 65                  70                  75                  80

Gln Met Asn Ser Leu Arg Ala Glu Asp Thr Ala Thr Tyr Tyr Cys Ala
                85                  90                  95

Tyr Ser Ser Trp Gln Pro Tyr Val Ser Tyr Trp Gly Gln Gly Thr Gln
            100                 105                 110

Val Thr Val Ser Ser
            115

<210> SEQ ID NO 66
<211> LENGTH: 124
<212> TYPE: PRT
<213> ORGANISM: Artificial
<220> FEATURE:
<223> OTHER INFORMATION: Synthetic 4SNP61

<400> SEQUENCE: 66

Val Gln Leu Gln Ala Ser Gly Gly Gly Phe Val Gln Pro Gly Gly Ser
 1               5                  10                  15

Leu Arg Leu Ser Cys Ala Ala Ser Gly Phe Thr Ser Thr Ser Thr Val
                20                  25                  30

Met Gly Trp Phe Arg Gln Ala Pro Gly Lys Glu Arg Glu Phe Val Ser
            35                  40                  45

Ala Ile Ser Ser Ala His Thr Met Asp Thr Tyr Tyr Ala Asp Ser Val
        50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Thr Tyr Tyr Cys
                85                  90                  95

Ala Pro Ala Pro Met Leu Gly Gln Met Ile Thr Gln Pro Ala Leu Pro
            100                 105                 110

Tyr Trp Gly Gln Gly Thr Gln Val Thr Val Ser Ser
            115                 120

<210> SEQ ID NO 67
<211> LENGTH: 117
<212> TYPE: PRT
<213> ORGANISM: Artificial
<220> FEATURE:
<223> OTHER INFORMATION: Synthetic 4SP10

<400> SEQUENCE: 67

Val Gln Leu Gln Ala Ser Gly Gly Gly Phe Val Gln Pro Gly Gly Ser
 1               5                  10                  15

Leu Arg Leu Ser Cys Ala Ala Ser Gly Arg Phe Trp Arg Arg Tyr Thr
                20                  25                  30

Met Gly Trp Phe Arg Gln Ala Pro Gly Lys Glu Arg Glu Phe Val Ser
            35                  40                  45

Ala Ile Ser Gly Thr Ser Asp Trp Thr Tyr Tyr Ala Asp Ser Val Lys
        50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Thr Tyr Tyr Cys Ala
                85                  90                  95
```

Pro Pro His Phe Ser Gly Ala Ala Ile Tyr Trp Gly Gln Gly Thr Gln
            100                 105                 110

Val Thr Val Ser Ser
        115

<210> SEQ ID NO 68
<211> LENGTH: 123
<212> TYPE: PRT
<213> ORGANISM: Artificial
<220> FEATURE:
<223> OTHER INFORMATION: Synthetic 5SP11

<400> SEQUENCE: 68

Val Gln Leu Gln Ala Ser Gly Gly Gly Phe Val Gln Pro Gly Gly Ser
1               5                   10                  15

Leu Arg Leu Ser Cys Ala Ala Ser Gly Ala Gly Trp Arg Ala Glu Ala
            20                  25                  30

Met Gly Trp Phe Arg Gln Ala Pro Gly Lys Glu Arg Glu Phe Val Ser
        35                  40                  45

Ala Ile Ser Ser Asp Gly Asp His Thr Ile Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ile Met Gln Thr Gln Met Arg Arg Thr Ser Asp Tyr Arg Phe Tyr
            100                 105                 110

Trp Gly Gln Gly Thr Gln Val Thr Val Ser Ser
        115                 120

<210> SEQ ID NO 69
<211> LENGTH: 125
<212> TYPE: PRT
<213> ORGANISM: Artificial
<220> FEATURE:
<223> OTHER INFORMATION: Synthetic 5SP58

<400> SEQUENCE: 69

Val Gln Leu Gln Ala Ser Gly Gly Gly Phe Val Gln Pro Gly Gly Ser
1               5                   10                  15

Leu Arg Leu Ser Cys Ala Ala Ser Gly Asp Thr Phe Ser Asp Asp Val
            20                  25                  30

Met Gly Trp Phe Arg Gln Ala Pro Gly Lys Glu Arg Glu Phe Val Ser
        35                  40                  45

Ala Ile Ser Asp Trp Pro Thr Thr Gln Ser Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Gln Ala Asn Gly Asp His Ser Tyr Pro Leu Trp Lys Tyr Gly Asn
            100                 105                 110

Met Tyr Trp Gly Gln Gly Thr Gln Val Thr Val Ser Ser
        115                 120                 125

<210> SEQ ID NO 70
<211> LENGTH: 121
<212> TYPE: PRT
<213> ORGANISM: Artificial

<220> FEATURE:
<223> OTHER INFORMATION: Synthetic 5SNP47

<400> SEQUENCE: 70

Val Gln Leu Gln Ala Ser Gly Gly Gly Phe Val Gln Pro Gly Gly Ser
1               5                   10                  15

Leu Arg Leu Ser Cys Ala Ala Ser Gly Arg Thr Ser Arg Phe Tyr Ser
            20                  25                  30

Met Gly Trp Phe Arg Gln Ala Pro Gly Lys Glu Arg Glu Phe Val Ser
        35                  40                  45

Ala Ile Ser Phe Asn Ser Asp Tyr Phe Leu Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Trp Trp Tyr Arg Tyr Thr Glu Gly Met Thr Met Tyr Trp Gly
            100                 105                 110

Gln Gly Thr Gln Val Thr Val Ser Ser
        115                 120

<210> SEQ ID NO 71
<211> LENGTH: 124
<212> TYPE: PRT
<213> ORGANISM: Artificial
<220> FEATURE:
<223> OTHER INFORMATION: Synthetic 5SNP48

<400> SEQUENCE: 71

Val Gln Leu Gln Ala Ser Gly Gly Gly Phe Val Gln Pro Gly Gly Ser
1               5                   10                  15

Leu Arg Leu Ser Cys Ala Ala Ser Gly Thr Ser Trp Phe Thr Glu Val
            20                  25                  30

Met Gly Trp Phe Arg Gln Ala Pro Gly Lys Glu Arg Glu Phe Val Ser
        35                  40                  45

Ala Ile Ser Gly Leu His Asp Val Gly Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Leu Asp Lys Trp Tyr Thr Lys Ala Met Asp Ala Arg Lys Asp
            100                 105                 110

Tyr Trp Gly Gln Gly Thr Gln Val Thr Val Ser Ser
        115                 120

<210> SEQ ID NO 72
<211> LENGTH: 121
<212> TYPE: PRT
<213> ORGANISM: Artificial
<220> FEATURE:
<223> OTHER INFORMATION: Synthetic 5SNP65

<400> SEQUENCE: 72

Val Gln Leu Gln Ala Ser Gly Gly Gly Phe Val Gln Pro Gly Gly Ser
1               5                   10                  15

Leu Arg Leu Ser Cys Ala Ala Ser Gly Ala Thr Tyr Glu Gly Glu Ala
            20                  25                  30

Met Gly Trp Phe Arg Gln Ala Pro Gly Lys Glu Arg Glu Phe Val Ser
            35                  40                  45

Ala Ile Ser Ser Tyr Pro Ser Val Ile Ser Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Thr Tyr Tyr Cys
                 85                  90                  95

Ala Tyr Trp Val Asn His Glu Gly Thr Ile Arg Glu Ile Tyr Trp Gly
                100                 105                 110

Gln Gly Thr Gln Val Thr Val Ser Ser
            115                 120

<210> SEQ ID NO 73
<211> LENGTH: 124
<212> TYPE: PRT
<213> ORGANISM: Artificial
<220> FEATURE:
<223> OTHER INFORMATION: Synthetic 6

<400> SEQUENCE: 73

Val Gln Leu Gln Ala Ser Gly Gly Gly Phe Val Gln Pro Gly Gly Ser
 1               5                  10                  15

Leu Arg Leu Ser Cys Ala Ala Ser Gly Tyr Gly Ser Thr Ile Glu Thr
                 20                  25                  30

Met Gly Trp Phe Arg Gln Ala Pro Gly Lys Glu Arg Glu Phe Val Ser
            35                  40                  45

Ala Ile Ser Arg Ala Pro Gly Pro Ser Gln Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Thr Tyr Tyr Cys
                 85                  90                  95

Ala Pro Ile Asn Asn Arg Thr Met Gln Asp Ser Met Phe Leu Trp Asn
                100                 105                 110

Tyr Trp Gly Gln Gly Thr Gln Val Thr Val Ser Ser
            115                 120

<210> SEQ ID NO 74
<211> LENGTH: 124
<212> TYPE: PRT
<213> ORGANISM: Artificial
<220> FEATURE:
<223> OTHER INFORMATION: Synthetic 20

<400> SEQUENCE: 74

Val Gln Leu Gln Ala Ser Gly Gly Gly Phe Val Gln Pro Gly Gly Ser
 1               5                  10                  15

Leu Arg Leu Ser Cys Ala Ala Ser Gly Thr Thr Ser Phe Trp Tyr Thr
                 20                  25                  30

Met Gly Trp Phe Arg Gln Ala Pro Gly Lys Glu Arg Glu Phe Val Ser
            35                  40                  45

Ala Ile Ser Trp Arg Phe Asn Thr Thr Thr Tyr Tyr Ala Asp Ser Val
 50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Thr Tyr Tyr Cys
                 85                  90                  95

Ala Ile Pro Arg Tyr Ser Leu Asp Ala Val Pro His Arg Ala Ser Thr
            100                 105                 110

Tyr Trp Gly Gln Gly Thr Gln Val Thr Val Ser Ser
        115                 120

<210> SEQ ID NO 75
<211> LENGTH: 124
<212> TYPE: PRT
<213> ORGANISM: Artificial
<220> FEATURE:
<223> OTHER INFORMATION: Synthetic 15

<400> SEQUENCE: 75

Val Gln Leu Gln Ala Ser Gly Gly Gly Phe Val Gln Pro Gly Gly Ser
1               5                   10                  15

Leu Arg Leu Ser Cys Ala Ala Ser Gly Ser Tyr Ser Arg Gly Glu Thr
            20                  25                  30

Met Gly Trp Phe Arg Gln Ala Pro Gly Lys Glu Arg Glu Phe Val Ser
        35                  40                  45

Ala Ile Ser Asp Thr His Asn Tyr Glu Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Ser Pro Gln Phe His Lys Ile Met Lys Gly Ser Gln Val Gly
            100                 105                 110

Tyr Trp Gly Gln Gly Thr Gln Val Thr Val Ser Ser
        115                 120

<210> SEQ ID NO 76
<211> LENGTH: 121
<212> TYPE: PRT
<213> ORGANISM: Artificial
<220> FEATURE:
<223> OTHER INFORMATION: Synthetic 5

<400> SEQUENCE: 76

Val Gln Leu Gln Ala Ser Gly Gly Gly Phe Val Gln Pro Gly Gly Ser
1               5                   10                  15

Leu Arg Leu Ser Cys Ala Ala Ser Gly Ala Thr Ser Gly Gly Thr Val
            20                  25                  30

Met Gly Trp Phe Arg Gln Ala Pro Gly Lys Glu Arg Glu Phe Val Ser
        35                  40                  45

Ala Ile Ser Arg Ser Gln Thr Lys Ala Thr Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Pro Met Glu His Glu Ala Leu Lys Gln His Pro Leu Tyr Trp Gly
            100                 105                 110

Gln Gly Thr Gln Val Thr Val Ser Ser
        115                 120

<210> SEQ ID NO 77
<211> LENGTH: 124
<212> TYPE: PRT

<213> ORGANISM: Artificial
<220> FEATURE:
<223> OTHER INFORMATION: Synthetic 71

<400> SEQUENCE: 77

Val Gln Leu Gln Ala Ser Gly Gly Gly Phe Val Gln Pro Gly Gly Ser
1               5                   10                  15

Leu Arg Leu Ser Cys Ala Ala Ser Gly Asp Gly Ser Asp Gly Asp Val
                20                  25                  30

Met Gly Trp Phe Arg Gln Ala Pro Gly Lys Glu Arg Glu Phe Val Ser
            35                  40                  45

Ala Ile Ser Arg Tyr Pro Gly Arg Ser Pro Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ala Arg Trp Ile Ser Arg Lys Trp Tyr Thr Thr Pro Phe Gln Gly
            100                 105                 110

Tyr Trp Gly Gln Gly Thr Gln Val Thr Val Ser Ser
        115                 120

<210> SEQ ID NO 78
<211> LENGTH: 118
<212> TYPE: PRT
<213> ORGANISM: Artificial
<220> FEATURE:
<223> OTHER INFORMATION: Synthetic E3

<400> SEQUENCE: 78

Val Gln Leu Gln Ala Ser Gly Gly Gly Phe Val Gln Pro Gly Gly Ser
1               5                   10                  15

Leu Arg Leu Ser Cys Ala Ala Ser Gly Ser Thr Tyr Glu Thr Tyr Ala
                20                  25                  30

Met Gly Trp Phe Arg Gln Ala Pro Gly Lys Glu Arg Glu Phe Val Ser
            35                  40                  45

Ala Ile Ser Ala Ser Pro Thr Ile Glu Gly Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Thr Trp Ser Lys Met Gly Ile Ser Ile Tyr Trp Gly Gln Gly Thr
            100                 105                 110

Gln Val Thr Val Ser Ser
        115

<210> SEQ ID NO 79
<211> LENGTH: 121
<212> TYPE: PRT
<213> ORGANISM: Artificial
<220> FEATURE:
<223> OTHER INFORMATION: Synthetic A6

<400> SEQUENCE: 79

Val Gln Leu Gln Ala Ser Gly Gly Gly Phe Val Gln Pro Gly Gly Ser
1               5                   10                  15

Leu Arg Leu Ser Cys Ala Ala Ser Gly Asp Thr Trp Asp Gln Tyr Val
                20                  25                  30

Met Gly Trp Phe Arg Gln Ala Pro Gly Lys Glu Arg Glu Phe Val Ser
            35                  40                  45

Ala Ile Ser Arg Ser Gly Thr His Gly Ile Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Pro Leu Thr His Gln Trp Met Gly Arg Thr Phe Pro Tyr Trp Gly
            100                 105                 110

Gln Gly Thr Gln Val Thr Val Ser Ser
        115                 120

<210> SEQ ID NO 80
<211> LENGTH: 118
<212> TYPE: PRT
<213> ORGANISM: Artificial
<220> FEATURE:
<223> OTHER INFORMATION: Synthetic G12

<400> SEQUENCE: 80

Val Gln Leu Gln Ala Ser Gly Gly Gly Phe Val Gln Pro Gly Gly Ser
1               5                   10                  15

Leu Arg Leu Ser Cys Ala Ala Ser Gly Arg Thr Ser Gly Trp Tyr Ala
            20                  25                  30

Met Gly Trp Phe Arg Gln Ala Pro Gly Lys Glu Arg Glu Phe Val Ser
            35                  40                  45

Ala Ile Ser Ser Arg Ala Ser Ser Gln Glu Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Val Trp Met Lys Met Gly Ile Glu Ile Tyr Trp Gly Gln Gly Thr
            100                 105                 110

Gln Val Thr Val Ser Ser
        115

<210> SEQ ID NO 81
<211> LENGTH: 7
<212> TYPE: PRT
<213> ORGANISM: Artificial
<220> FEATURE:
<223> OTHER INFORMATION: Synthetic CDR1-NB61

<400> SEQUENCE: 81

Thr Thr Trp Phe Asn Glu Val
1               5

<210> SEQ ID NO 82
<211> LENGTH: 7
<212> TYPE: PRT
<213> ORGANISM: Artificial
<220> FEATURE:
<223> OTHER INFORMATION: Synthetic CDR2-NB61

<400> SEQUENCE: 82

Gly Ser Thr Ser Trp Ala Glu
1               5

```
<210> SEQ ID NO 83
<211> LENGTH: 15
<212> TYPE: PRT
<213> ORGANISM: Artificial
<220> FEATURE:
<223> OTHER INFORMATION: Synthetic CDR3-NB61

<400> SEQUENCE: 83

Arg Met Ser Phe Met Arg Ala Gly Arg Thr Pro Met Thr Pro Met
1               5                   10                  15

<210> SEQ ID NO 84
<211> LENGTH: 7
<212> TYPE: PRT
<213> ORGANISM: Artificial
<220> FEATURE:
<223> OTHER INFORMATION: Synthetic CDR1-212B

<400> SEQUENCE: 84

Asp Thr Trp Trp Ser Ser Ala
1               5

<210> SEQ ID NO 85
<211> LENGTH: 7
<212> TYPE: PRT
<213> ORGANISM: Artificial
<220> FEATURE:
<223> OTHER INFORMATION: Synthetic CDR2-212B

<400> SEQUENCE: 85

Phe Tyr Pro Thr Glu Tyr Thr
1               5

<210> SEQ ID NO 86
<211> LENGTH: 12
<212> TYPE: PRT
<213> ORGANISM: Artificial
<220> FEATURE:
<223> OTHER INFORMATION: Synthetic CDR3-212B

<400> SEQUENCE: 86

Trp Ile Ala Trp Gly Pro Trp Met Arg Thr Ser Trp
1               5                   10

<210> SEQ ID NO 87
<211> LENGTH: 7
<212> TYPE: PRT
<213> ORGANISM: Artificial
<220> FEATURE:
<223> OTHER INFORMATION: Synthetic CDR1-111B

<400> SEQUENCE: 87

Gly Thr Ser Lys Gln Tyr Gly
1               5

<210> SEQ ID NO 88
<211> LENGTH: 7
<212> TYPE: PRT
<213> ORGANISM: Artificial
<220> FEATURE:
<223> OTHER INFORMATION: Synthetic CDR2-111B

<400> SEQUENCE: 88

Arg Gln Glu Gly Glu Thr Ile
1               5
```

<210> SEQ ID NO 89
<211> LENGTH: 9
<212> TYPE: PRT
<213> ORGANISM: Artificial
<220> FEATURE:
<223> OTHER INFORMATION: Synthetic CDR3-111B

<400> SEQUENCE: 89

Tyr Arg His Val Trp Pro Tyr Pro Glu
1               5

<210> SEQ ID NO 90
<211> LENGTH: 7
<212> TYPE: PRT
<213> ORGANISM: Artificial
<220> FEATURE:
<223> OTHER INFORMATION: Synthetic DR1-404F

<400> SEQUENCE: 90

Arg Thr Ser Lys Asn Tyr Ala
1               5

<210> SEQ ID NO 91
<211> LENGTH: 7
<212> TYPE: PRT
<213> ORGANISM: Artificial
<220> FEATURE:
<223> OTHER INFORMATION: Synthetic CDR2-404F

<400> SEQUENCE: 91

Trp Thr Thr Asn Gln Asp Thr
1               5

<210> SEQ ID NO 92
<211> LENGTH: 9
<212> TYPE: PRT
<213> ORGANISM: Artificial
<220> FEATURE:
<223> OTHER INFORMATION: Synthetic CDR3-404F

<400> SEQUENCE: 92

Ile Trp Asp Lys Arg Glu Ile Ser Ile
1               5

<210> SEQ ID NO 93
<211> LENGTH: 124
<212> TYPE: PRT
<213> ORGANISM: Artificial
<220> FEATURE:
<223> OTHER INFORMATION: Synthetic NB61

<400> SEQUENCE: 93

Val Gln Leu Gln Ala Ser Gly Gly Gly Phe Val Gln Pro Gly Gly Ser
1               5                   10                  15

Leu Arg Leu Ser Cys Ala Ala Ser Gly Thr Thr Trp Phe Asn Glu Val
            20                  25                  30

Met Gly Trp Phe Arg Gln Ala Pro Gly Lys Glu Arg Glu Phe Val Ser
        35                  40                  45

Ala Ile Ser Gly Ser Thr Ser Trp Ala Glu Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
            85                  90                  95

Ala Arg Met Ser Phe Met Arg Ala Gly Arg Thr Pro Thr Pro Met
            100                 105                 110
Tyr Trp Gly Gln Gly Thr Gln Val Thr Val Ser Ser
            115                 120

<210> SEQ ID NO 94
<211> LENGTH: 121
<212> TYPE: PRT
<213> ORGANISM: Artificial
<220> FEATURE:
<223> OTHER INFORMATION: Synthetic 212B

<400> SEQUENCE: 94

Val Gln Leu Gln Ala Ser Gly Gly Gly Phe Val Gln Pro Gly Gly Ser
1               5                   10                  15
Leu Arg Leu Ser Cys Ala Ala Ser Gly Asp Thr Trp Trp Ser Ser Ala
            20                  25                  30
Met Gly Trp Phe Arg Gln Ala Pro Gly Lys Glu Arg Glu Phe Val Ser
            35                  40                  45
Ala Ile Ser Phe Tyr Pro Thr Glu Tyr Thr Tyr Tyr Ala Asp Ser Val
        50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Thr Tyr Tyr Cys
                85                  90                  95
Ala Trp Ile Ala Trp Gly Pro Trp Met Arg Thr Ser Trp Tyr Trp Gly
            100                 105                 110
Gln Gly Thr Gln Val Thr Val Ser Ser
            115                 120

<210> SEQ ID NO 95
<211> LENGTH: 118
<212> TYPE: PRT
<213> ORGANISM: Artificial
<220> FEATURE:
<223> OTHER INFORMATION: Synthetic 111B

<400> SEQUENCE: 95

Val Gln Leu Gln Ala Ser Gly Gly Gly Phe Val Gln Pro Gly Gly Ser
1               5                   10                  15
Leu Arg Leu Ser Cys Ala Ala Ser Gly Gly Thr Ser Lys Gln Tyr Gly
            20                  25                  30
Met Gly Trp Phe Arg Gln Ala Pro Gly Lys Glu Arg Glu Phe Val Ser
            35                  40                  45
Ala Ile Ser Arg Gln Glu Gly Glu Thr Ile Tyr Tyr Ala Asp Ser Val
        50                  55                  60
Lys Gly Arg Phe Thr Ile Ser Arg Asp Asn Ser Lys Asn Thr Val Tyr
65                  70                  75                  80
Leu Gln Met Asn Ser Leu Arg Ala Glu Asp Thr Ala Thr Tyr Tyr Cys
                85                  90                  95
Ala Tyr Arg His Val Trp Pro Tyr Pro Glu Tyr Trp Gly Gln Gly Thr
            100                 105                 110
Gln Val Thr Val Ser Ser
        115

<210> SEQ ID NO 96
<211> LENGTH: 118
<212> TYPE: PRT
<213> ORGANISM: Artificial

```
<220> FEATURE:
<223> OTHER INFORMATION: Synthetic 404F

<400> SEQUENCE: 96

Val Gln Leu Gln Ala Ser Gly Gly Phe Val Gln Pro Gly Gly Ser
1               5                   10                  15

Leu Arg Leu Ser Cys Ala Ala Ser Gly Arg Thr Ser Lys Asn Tyr Ala
                20                  25                  30

Met Gly Trp Phe Arg Gln Ala Pro Gly Lys Glu Arg Glu Phe Val Ser
            35                  40                  45

Ala Ile Ser Trp Thr Thr Asn Gln Asp Thr Tyr Tyr Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Thr Tyr Tyr Cys
                85                  90                  95

Ala Ile Trp Asp Lys Arg Glu Ile Ser Ile Tyr Trp Gly Gln Gly Thr
            100                 105                 110

Gln Val Thr Val Ser Ser
            115
```